(12) United States Patent
Hils et al.

(10) Patent No.: US 8,808,980 B2
(45) Date of Patent: Aug. 19, 2014

(54) STABILIZED OPEN FORM TRANSGLUTAMINASE AS A DIAGNOSTIC INDICTOR FOR AUTOIMMUNE DISEASES

(75) Inventors: Martin Hils, Damstadt (DE); Ralf Pasternack, Griesheim (DE); Johannes Weber, Darmstadt (DE)

(73) Assignee: Zedira GmbH, Darmstadt (DE)

( * ) Notice: Subject to any disclaimer, the term of this patent is extended or adjusted under 35 U.S.C. 154(b) by 0 days.

(21) Appl. No.: 13/509,225

(22) PCT Filed: Nov. 11, 2010

(86) PCT No.: PCT/EP2010/006983
§ 371 (c)(1),
(2), (4) Date: Aug. 20, 2012

(87) PCT Pub. No.: WO2011/057826
PCT Pub. Date: May 19, 2011

(65) Prior Publication Data
US 2012/0315262 A1 Dec. 13, 2012

Related U.S. Application Data

(60) Provisional application No. 61/282,008, filed on Dec. 2, 2009.

(30) Foreign Application Priority Data

Nov. 11, 2009 (EP) .................................... 09014100
Jun. 23, 2010 (EP) .................................... 10007682

(51) Int. Cl.
*C12Q 1/00* (2006.01)
(52) U.S. Cl.
USPC .......................................................... 435/4
(58) Field of Classification Search
USPC .......................................................... 435/4
See application file for complete search history.

(56) References Cited

U.S. PATENT DOCUMENTS

2013/0045493 A1* 2/2013 Korponay-Szabo et al. 435/7.93

FOREIGN PATENT DOCUMENTS

EP 1978364 10/2008

OTHER PUBLICATIONS

Pardin C. et al. Photolabeling of Tissue TG Reveals the Binding Mode of Potent Cinnamoyl Inhibitors. Biochemistry 48(15)3346-3353, Apr. 2009.*
Pinkas D. et al. Transglutaminase 2 Undergoes a Large Conformational Change upon Activation. PLoS Biology 5(12)2788-2796, Dec. 2007.*
International Search Report/Written Opinion for PCT Application No. PCT/EP2010/006983 issued Dec. 21, 2010.
Seissler J et al "Autoantibodies from patients with coeliac disease recognize distinct functional domains of the autoantigen tissue transglutaminase", Clinical and Experimental Immunology, vol. 125, Aug. 25, 2001, pp. 216-221.
Pinkas, D.M. et al "Transglutaminase 2 undergoes a large conformational change upon activation", PLOS Biology, vol. 5, No. 12, Dec. 2007, pp. 2788-2795.
Pardin Christophe et al "Photolabeling of Tissue Transglutaminase Reveals the Binding Mode of Potent Cinnamoyl Inhibitors", Biochemistry, vol. 48, No. 15, Apr. 1, 2009, pp. 3346-3353. (Abstract).

* cited by examiner

*Primary Examiner* — Ralph Gitomer
(74) *Attorney, Agent, or Firm* — Meyertons, Hood, Kivlin, Kowert & Goetzel, P.C.; Eric B. Meyertons

(57) ABSTRACT

The present invention relates to the diagnosis of disorders or dysfunctions characterized by autoimmune responses to the enzyme class of transglutaminases. The present invention provides a novel open structure of the transglutaminases in a stabilized form which renders new epitopes accessible for antibody-binding.

5 Claims, 5 Drawing Sheets

STABILIZED OPEN FORM TRANSGLUTAMINASE AS A DIAGNOSTIC INDICTOR FOR AUTOIMMUNE DISEASES

PRIORITY CLAIM

This application is a 371 of PCT Application PCT/EP2010/006983, filed Nov. 11, 2010, which claims priority to U.S. Provisional Application Ser. No. 61/282,008, filed Dec. 2, 2009.

BACKGROUND OF THE INVENTION

1. Field of the Invention

The present invention relates to the diagnosis of disorders or dysfunctions characterized by autoimmune responses to the enzyme class of transglutaminases. The present invention provides a novel open structure of the transglutaminases in a stabilized form which renders new epitopes accessible for antibody-binding.

2. Description of the Relevant Art

Transglutaminases (TG) are enzymes that exist in higher vertebrates including the human body as a family of nine members, including the inactive structural protein band 4.2. They fulfil a large variety of physiological functions e.g. in coagulation, inflammation, cell differentiation, apoptosis, cell-cell and cell-matrix interactions, and wound healing. In the presence of $Ca^{2+}$ transglutaminases may develop their catalytic activity, the formation of inter- and intra-molecular γ-glutamyl-ε-lysine bonds, also called iso-peptide bonds, between the side chains of peptidic glutamine and lysine. In general the results of this activity are high-molecular weight protein aggregates. Transglutaminases 1, 3 and 5 are mainly involved in skin-formation, factor XIII (plasma-transglutaminase) is active in blood coagulation and wound healing, transglutaminase 6 has mainly been found in neuronal tissues and transglutaminase 4 in semen fluid. Transglutaminase 2 (tissue transglutaminase, TG2) is ubiquitously present in various tissues. Besides its cross-linking activity TG2 may also deamidate the carboxyamide group of peptidic glutamine, especially under slightly acidic conditions as well as in the absence of lysine or other primary amines. As the deamidation product is a carboxyl group, a negative charge is introduced into the peptide which results in a significant change of peptide properties. Further TG2 has GTP-hydrolysing activity and functions as a G-Protein. Even kinase activity is described. TG2 plays a role in several diseases like celiac disease, fibrosis, cancer, and neurological disorders.

In celiac disease, a chronic inflammation of the small intestine and an autoimmune disease, TG2 plays a multifunctional role. Digestion of proteins present in our food is performed by proteolytical cleavage to amino acids and small peptides, which can be resorbed by the intestinal mucosa. Cereal proteins like gluten show a high content of the amino acid proline. But the enzymes responsible for protein degradation in the digestive tract are not able to hydrolyse proline-rich proteins into amino acids and small peptides. Consequently rather long peptides, like gliadin peptides are present in the mucosa. Due to their size they cannot be resorbed, but they are still able to pass the epithelium and to reach the so called lamina propria, a connecting tissue between epithelium and muscular tissue. In the lamina propria extracellular TG2 is present. Now an essential step in celiac disease pathophysiology takes place: TG2 deamidates gliadin peptides. In their deamidated form gliadin peptides are recognized by the HLA-DQ2 and HLA-DQ8 receptors of immune cells. This recognition leads to the triggering of the inflammatory response which in the final stage of the disease manifests in a complete villous atrophy of the intestinal mucosa. TG2 not only catalyses gliadin deamidation, it serves also as autoantigen in celiac disease. Patients who suffer from celiac disease develop autoantibodies against TG2. If patients successfully follow a strict gluten free diet anti-TG2-autoantibody titers decrease. Therefore TG2 is not only used as antigen for autoantibody-detection in the diagnosis of celiac disease, but also in the follow up and control of the gluten free diet. TG2-autoantibodies are also found in other diseases like diabetes type 1 or psoriasis and may therefore be used in non-celiac disease diagnostics too.

Interestingly in other indications developing along or in consequence to celiac disease further autoantibodies against transglutaminases can be found: Dermatitis herpetiformis, a gluten sensitive skin disorder is characterized by the presence of autoantibodies against epidermal transglutaminase (TG3) whereas in glutensensitive ataxia autoantibodies against neuronal transglutaminase (TG6) have been found.

Objective of the present invention is to provide a more sensitive method for detecting autoimmune diseases characterized by the presence of transglutaminase specific autoantibodies.

The objective of the present invention is solved by the teaching of the independent claims. Further advantageous features, aspects and details of the invention are evident from the dependent claims, the description, the figures and the examples of the present application.

SUMMARY OF THE INVENTION

The present invention surprisingly found, that the use of the open form transglutaminase for detection of autoantibodies leads to higher titers compared to the closed form of the transglutaminase and reveals positive titers in patients with titers against the closed TG form below the cut-off. This invention is of immense impact on diagnosis, antibody isolation and immune cell characterization.

The transglutaminases change their tertiary structure upon substrate binding. Inactive non-substrate binding TG shows a closed form which upon substrate binding changes to an open form. Both forms the closed form without substrate and the open form with substrate are recognized by autoantibodies. It is assumed that autoantibodies for the closed form as well as for the open form exist.

However it was most surprisingly found that the open form of the TG can be used to detect autoantibodies in much higher sensitivity in comparison to the closed form. Consequently, much more sensitive and precise methods for detecting autoantibodies against the open form of the TG were developed and are subject of the present invention in order to much more precisely detect and diagnose diseases associated with the presence of autoantibodies for the open form transglutaminase.

Thus the present invention relates to a method for the diagnosis of an autoimmune disorder or an intestinal disorder or a skin disorder or a neurological disorder or other diseases, wherein the open form transglutaminase or antigenically active fragments of the open form transglutaminase are used for the detection of the presence of autoantibodies specific for the open form transglutaminase or antigenically active fragments of the open form transglutaminase.

The open form of the transglutaminase or a fragment of the open form of a transglutaminase which has comparable activity to the open form transglutaminase, thus an antigenically active fragment of this open form transglutaminase is generated by reacting the transglutaminase or the antigenically active fragment of the transglutaminase with an inhibitor comprising a backbone, a peptide backbone or a peptidomimetic backbone and a thiol reactive group able to form a covalent bond to the thiol group of the cysteine in the active site of the TG. The inhibitor might also react with other cysteines which are not located in the active side of the TG but the inhibitor must be able to react with the cysteine in the active site of the respective TG. In order to make the inhibitor more regioselective, the thiol reactive group of the inhibitor is preferably attached to a backbone, a peptide backbone or peptidomimetic backbone or any synthetic backbone which has affinity to the active site in order to increase regioselectivity of the inhibitor molecule. In order to generate the open form of a TG it is important that the inhibitor attaches covalently to the thiol group of the cysteine within the active site of the TG. Consequently, inhibitors are preferred which have a backbone attached to a thiol reactive group which has certain similarity to the natural substrates of the TG. Such backbones are preferably peptide-like backbones, i.d. backbones which comprise amide bonds and at least one carbon chain attached to the carbonyl group of the amide bond or at least one optionally substituted carbon atom between two amide bonds.

The autoimmune disorder can be selected from the group comprising or consisting of Addisons's disease, alopecia areata, ankylosing spondylitis, antiphosholipid antibody syndrome, autoimmune hemolytic anemia, autoimmune hepatitis, autoimmune inner ear disease, autoimmune lymphoproliferative syndrome, autoimmune thrombocytopenic purpura, immune thrombocytopenic purpura, balo disease, Behcet's disease, bullous pemphigoid, cardiomyopathy, chronic fatigue immune dysfunction syndrome, chronic inflammatory demyelinating polyneuropathy, Cicatricial pemphigoid, cold agglutinin disease, CREST syndrome, Crohn's disease, Degos disease, dermatomyositis, dermatomyositis-juvenile, discoid lupus, essential mixed cryoglobulinemia, fibromyalgia, Goodpasture's syndrome, Graves disease, Guillain-Baré, Hashimoto thyroiditis, idiopathic pulmonary fibrosis, idiopathic thrombocytopenia purpura, IgA nephropathy, insulin-dependent diabetes, juvneile arthritis, lichen planus, lupus, Ménière disease, mixed connective tissue disease, multiple sclerosis, myasthenia gravis, PANDAS, pemphigus vulgaris, pernicious anemia, polyarteritis nodosa, polychondritis, polyglandular syndromes, polymyalgia rheumatica, polymyositis, dermatomyositis, primary agammaglobulinemia, primary biliary cirrhosis, psoriasis, Raynaud phenomenon, Reiter's syndrome, rheumatic fever, rheumatoid arthritis, sarcoidosis, scleroderma, sclerosing cholangitis, Sjögren's syndrome, Takayasu's arteritis, temporal arteritis, giant cell arteritis, ulcerative colitis, uveitis vasuclitis, vitiligo, Wegener's granulomatosis, neurological disorder, paraneoplastic neurological syndrome, cereal protein sensitivity disorder, gluten sensitive disorders, celiac disease, dermatitis herpetiformis, Morbus Duhring, diabetes mellitus type 1, anxiety, depression, brainstem encephalitis, cerebral vasculitis, chorea, dementia, epilepsy, cerebral calcifications, headache with white matter abnormalities, neuromyotonia, myasthenia gravis, myopathy, neuropathy, progressive multifocal leukoencephalopathy, progressive myoclonic encephalopathy, schizophreniform disorder, stiff-person syndrome, ataxia, ataxia with myoclonus, encephalitis, polymyositis, epilepsy with occipital cerebral calcifications, loss of sensation or muscle weakness, paraneoplastic cerebellar degeneration, paraneoplastic encephalomyelitis, paraneoplastic opsoclonus-myoclonus, cancer associated retinopathy, paraneoplastic stiff-man syndrome, paraneoplastic necrotizing myelopathy, a motor neuron syndrome, amyotrophic lateral sclerosis, subacute motor neuronopathy, subacute sensory neuronopathy, brachial neuritis and neuromyotonia.

Preferably the autoimmune disorder can be selected from the group comprising or consisting of celiac disease, dermatitis herpetiformis, psoriasis, Addisons disease; autoimmune hepatitis; chronic inflammatory demyelinating polyneuropathy; Hashimoto's thyroiditis; rheumatoid arthritis; multiple sclerosis; Polymyositis; ulcerative colitis; diabetes mellitus type 1; epilepsy; stiff-person syndrome and neuropathy, especially gluten sensitive neuropathy, gluten sensitive ataxia; idiopathic sporadic ataxia and gluten ataxia with enteropathy.

The present invention is most useful for the diagnosis of an autoimmune disorder or autoimmune disease and especially of gluten sensitive disorders, celiac disease, dermatitis herpetiformis and gluten sensitive ataxia.

In other words the present invention relates to a method for the diagnosis of an autoimmune disorder, wherein at least one open form transglutaminase or at least one antigenically active fragment of the open form transglutaminase is used for the detection of the presence of autoantibodies specific for the open form transglutaminase or specific for the antigenically active fragment of the open form transglutaminase. Further the at least one open form or inhibited transglutaminase or at least one antigenically active fragment of the open form or inhibited transglutaminase is used for the diagnosis of diseases or for the monitoring and assessment of the effectiveness of therapy, especially of autoimmune diseases. Further preferred is the use of open form TG, or an antigenically active fragment thereof, for detection of autoantibodies reacting with the open form TG in differential diagnosis of an autoimmune disease, preferably a cereal protein sensitivity disorder and in risk assessment for complications in individuals susceptible to cereal protein sensitivity disorder.

The transglutaminases or open form transglutaminases used within the inventive method are selected from the group comprising or consisting of TG1, TG2, TG3, TG4, TG5, TG6, TG7 or coagulation factor XIII.

Most proteins fold into unique 3-dimensional structures. The shape into which a protein naturally folds is known as its native conformation. But proteins are not entirely rigid molecules. Proteins may shift between several related structures while they perform their functions. In the context of these functional rearrangements, these tertiary or quaternary structures are usually referred to as "conformations", and transitions between them are called conformational changes. Such changes may be induced by the binding of a substrate molecule to an enzyme's active site, or the physical region of the protein that participates in chemical catalysis.

The term "open form transglutaminase" as used herein refers to a transglutaminase which underwent a conformational change after binding a substrate or an inhibitor so that the term "open form transglutaminase" refers to a transglutaminase with a substrate or an inhibitor bound to the transglutaminase and where the conformation of the transglutaminase changes when binding the substrate or inhibitor. Preferably the term "open form transglutaminase" refers to an extended or elongated protein conformation of a transglutaminase present during the time of binding a substrate or substrate analogue or inhibitor to the TG in contrary to the more globular conformation without a substrate or inhibitor bound. This closed form may bind a GDP. It is preferred to obtain and stabilize the open form of a transglutaminase using an inhibitor as a substrate analogue. Therefore the open form TG may also be referred to as substrate or inhibitor bound transglutaminase which undergoes a conformational change when binding the inhibitor. The change in conformation will last as long as the substrate or inhibitor is bound and will reversibly change back to the original closed conformation when the substrate or the reversible inhibitor is released. Thus, the "open form transglutaminases" of the present invention are these transglutaminases which underwent a change in conformation upon binding a substrate and preferably an irreversible inhibitor in order to stabilize this conformationally changed form.

The antigenically active fragments of the transglutaminases or of the open form transglutaminases are selected from the group comprising or consisting of antigenically active fragments of TG1, TG2, TG3, TG4, TG5, TG6, TG7 or coagulation factor XIII.

The term "antigenically active fragment" as used herein refers to a protein fragment that is able to elicit an antibody response and is able to be bound by an antibody. In regard to a TG or analogously to the open form of a TG, an "antigenically active fragment" can be further defined as an arrangement of amino acid residues forming part of the surface of the TG or open form TG, in particular the surfaces exposed upon enzyme activation, either in the form of a continuous peptide sequence or amino acids held together by an artificial backbone that mimics their arrangement in the native protein. An "antigenically active fragment" can also be a portion of a TG with proteins or derived peptides bound to its active site, which constitute common T cell epitopes. Examples for such proteins are proteins of the extracellular matrix like collagen, fibronectin, vitronectin, osteonectin or villamentin or plasma proteins like α2-antiplasmin, fibrin and fibrinogen or food-proteins like gliadin. An example for a gliadin derived peptide is the alpha-gliadin derived 33-mer LQLQPF-PQPQLPYPQPQLPYPQPQLPYPQPQPF [accession number AJ133612 (amino acids 57-89)]. Preferably the antigenically active fragment of an open from transglutaminase is a synthetic peptide.

Antigenically active fragments can be produced by several techniques. A convenient method is the production of truncated variants of the respective transglutaminase, by deleting N-terminal, C-terminal or internal amino acids or peptides at one or more positions with respect to the primary sequence. The resulting truncated transglutaminase can then be inhibited in order to convert it into its open conformation. In case that the truncated transglutaminase shows no enzymatic activity any more, a strong SH-reactive inhibitor may be used in order to convert the protein in its open conformation. A further method for the generation of antigenically active fragments is the usage of a synthetic peptide which covers the sequence around the active site cystein where an inhibitor is added by chemical methods to the active site cystein. Finally the open conformation transglutaminase may be treated with proteases in order to create antigenically active fragments, which can be separated by chromatographical methods known to people skilled in the art.

The methods of the present invention can also be performed using more than one open form or inhibited transglutaminase and/or more than one antigenically active fragment of the open form transglutaminase at the same time within the method. Thus, mixtures of transglutaminases (TGs) can be used within the inventive methods. Furthermore the detection of, for example, transglutaminase 2 autoantibodies or transglutaminase 3 autoantibodies or transglutaminase 6 autoantibodies can be combined with the detection of autoantibodies to one or more further transglutaminase isoforms such as TG1, TG3, TG4, TG5, TG6, TG7 or coagulation factor XIII.

In the following the invention is described in detail in regard to transglutaminase 2 (TG2) while the invention can be performed with all other TGs in a similar manner. However TG2, TG3 and TG6 are the preferred transglutaminases. Thus, the present invention is not limited to the use of TG2. TG2 is only used as representative example of all TGs for disclosing the present invention in detail.

The transglutaminase 2 changes its tertiary structure upon substrate binding. Whereas inactive non-substrate bound TG2 shows a closed more ball-shaped form, the two β-domains turn upon substrate binding resulting in a more longitudinal form as shown in FIG. 1. This shift in tertiary structure is a common feature of all vertebrate transglutaminases. Thus novel epitopes, which have been covered or masked in the closed form, are now accessible.

For instance, the tissue transglutaminase (TG2) is the autoantigen in celiac disease. The disease is characterized by an elevated titer of autoantibodies against TG2 (IgA and IgG). Although suffering from celiac disease, some patients show very low or no antibody titers at all. In a group of patients the lacking IgA-titer can be explained by a general IgA-deficiency. But there remain celiac disease patients with a biopsy proven celiac disease (intestinal villous atrophy) and without IgA-deficiency, but a TG2-autoantibody negative or doubtful serology.

Thus, the diseases described herein can be detected more precisely and accurate by the use of the open form TG for the detection of autoantibodies against or specifically against said open TG form.

The open form of the transglutaminase is present at the time of binding a substrate to the TG. The TG is in a closed form when no substrate is bound. In order to obtain the TG in its open form a substrate or an inhibitor is added to the TG. Since it is advantageous to obtain a TG stabilized in its open form, inhibitors and preferably irreversible inhibitors are used which react with the TG. Accordingly, in order to obtain the antigenically active fragment of the open form transglutaminase, the antigenically active fragment of the open form transglutaminase is reacted with an inhibitor and preferably an irreversible inhibitor in order to stabilize the open form of the antigenically active fragment of the open form transglutaminase.

As used herein, the term "irreversible inhibitor" refers to an inhibitor which covalently binds to the TG or which binds sufficiently tightly so that no equilibrium will exist. Irreversible inhibitors are most often inhibitors with at least one functional group which is able to form a covalent bond to the target such as a TG so that one inhibitor is required to inactivate one TG enzyme and consequently stabilize the open form of the TG.

Therefore the term "open form transglutaminase" or "inhibited transglutaminase" as used herein may also refer to transglutaminases with novel epitopes, which are only accessible for antibodies after binding of an inhibitor. The inventive method uses transglutaminases which allows detecting novel auto-antibodies which are not detected without the binding of an inhibitor. Therefore the inventive form of transglutaminases has newly accessible epitopes which allows for the detection of new auto-antibodies.

The terms "open form transglutaminase" and "open transglutaminase" and "inhibited transglutaminase" and "conformationally changed transglutaminase" is used herein as synonyms. These terms refer to a transglutaminase such as TG2, TG3, TG6 which change their conformation upon binding an inhibitor or a substrate so that two conformationally distinct transglutaminases exist which are recognized by two sorts of antibodies. The antibodies for the open form (or inhibited or conformationally changed form) do most probably not recognize the closed form. Both sorts of antibodies can be detected in order to diagnose autoimmune disorders characterized by the presence of autoantibodies against the two different forms (open/closed or respectively not inhibited/inhibited or conformationally unchanged/conformationally changed) of the respective transglutaminase.

The term "conformationally changed" refers to the changed conformation of the respective transglutaminase when a substrate or an inhibitor and especially one of the inhibitors disclosed herein is bound to the active site of the transglutaminase.

The closed form or not inhibited form or conformationally not changed form of the transglutaminase can be distinguished from the open form or inhibited form or conformationally changed form by the presence of another sort of autoantibodies directed to said open, inhibited or conformationally changed form. Therefore, presence of another sort of autoantibodies directed to one transglutaminase such as TG2 or TG3 or TG6 indicates that the open, inhibited or conformationally changed form of said transglutaminase exists.

Inhibitors based on proteins, e.g. proteins of the extracellular matrix, plasma-proteins or food-proteins, and dipeptidic or larger portions thereof as well as inhibitors comprising a peptide-like backbone, peptidomimetic backbone or any other backbone which has affinity to the active site of the TG or which has similarity with the backbone of the natural substrate in regard to length, number of atoms, tertiary structure, molecular weight, functional groups and/or polarity can be used for the production of the open form of transglutaminase 1, transglutaminase 2, transglutaminase 3, transglutaminase 4, transglutaminase 5, transglutaminase 6, transglutaminase 7 or the coagulation factor XIII.

Suitable inhibitors which are able to form covalent bonds to the TGs are inhibitors with thiol-reactive groups. Thiol-reactive groups are preferably such groups which are electrophil and which are able to undergo a nucleophilic addition reaction with the thiol group (—SH group) of cysteine such as acetylenes, electrophilic olefins, unsaturated aldimines, Michael acceptors, iodoacetamide, N-ethylmaleimide, parachloromercuribenzoic acid, alkyl isocyanates, 3,5-substituted-4,5-dihydroisoxazoles, oxiranes as described in U.S. Pat. No. 5,188,830, moreover imidazoles, pyrazoles, triazoles and tetrazoles as disclosed in U.S. Pat. No. 4,968,713, U.S. Pat. No. 5,019,572, U.S. Pat. No. 5,021,440, U.S. Pat. No. 5,030,644, U.S. Pat. No. 5,047,416, U.S. Pat. No. 5,077,285, U.S. Pat. No. 5,084,444, U.S. Pat. No. 5,098,707, U.S. Pat. No. 5,152,988 and U.S. Pat. No. 5,177,092, as well as the compound of the general formula

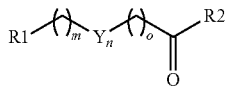

as disclosed in US 2002132776 A1 and other similar compounds with comparable reactivity in regard to thiol groups.

Preferred inhibitors which form covalent bonds to the TGs are inhibitors which comprise a peptide backbone or peptidomimetic backbone and a Michael acceptor moiety as reactive group. This Michael acceptor moiety is preferably a side chain bound to the peptidic or peptidomimetic backbone. Michael acceptor systems normally consist of a carbon-carbon double bond in conjugation to a carbonyl group.

Preferred inhibitors are represented by the general formula [TGI1]:

acceptor-substituted double bond-(CO)$_m$—C$_2$H$_4$-backbone [TGI1]

wherein m stands for 0 or 1 and preferably m is 0 and the acceptor-substituted double bond carries at least one electron-drawing residue capable to conjugate with an electronegativity ≥2.20 and the backbone is preferably a peptide or peptidomimetic from at least two amino acids and preferably a tetrapeptide or at least a dipeptidomimetic and/or the backbone shows at least one amide bond. The acceptor-substituted double bond is preferably a Michael system.

Further preferred inhibitors are represented by the general formula (I), (II) or (III):

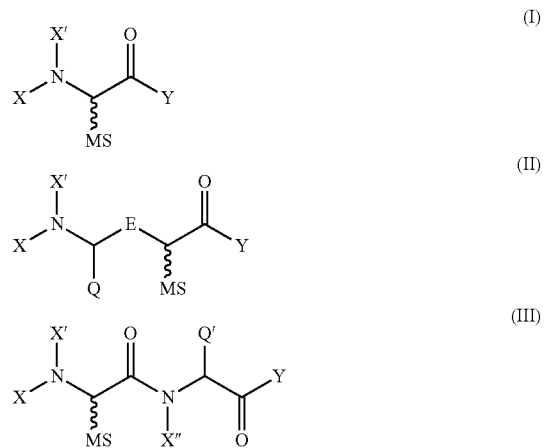

wherein
MS is the acceptor-substituted olefin of the

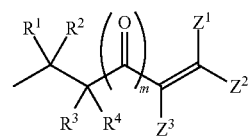

following structure:
E represents the following group —CH$_2$—, —CF$_2$—, —C$_2$H$_4$—, —CH$_2$—CF$_2$—, —CF$_2$—CH$_2$—, —CH=CH—, —CH(OH)—CH$_2$—, —C(=O)—CH$_2$—, —CH$_2$—NH—, —CH$_2$—O—, —CH(OH)—CH$_2$—NH—, —P(=O)(OH)—NH—, —P(=O)(OH)—O—, —P(=O)(OH)—S—, —P(=O)(OH)—CH$_2$—, —CH(OH)—CH$_2$—NH—, —C(=O)—NH—, —C(=O)—O— or —C(=O)—NX''—;
m is 0 or 1;
the residues Z$^1$, Z$^2$, Z$^3$ independently of each other represent the following groups: —CO—(C$_1$-C$_6$ alkyl), —CO—R$^6$, —CO—R$^7$, —CO—(C$_1$-C$_6$ halogenalkyl), —CO—(C$_3$-C$_{10}$ heteroaryl), —CO—(C$_6$-C$_{15}$ aryl), —COO—(C$_1$-C$_6$ halogenalkyl), —COO—(C$_3$-C$_{10}$ heteroaryl), —COO—(C$_6$-C$_{15}$ aryl), —COO—(C$_1$-C$_6$ alkyl), —COO—R$^8$, —COO—R$^9$, —CN, —F, —Cl, —COOH, —CO—NH(C$_1$-C$_6$ alkyl), —CO—N(C$_1$-C$_6$ alkyl)(C$_1$-C$_6$ alkyl), —CO—NR$^{10}$R$^{11}$, —CO—NH$_2$, —CO—N(CR$^{12}$R$^{13}$R$^{14}$)(CR$^{15}$R$^{16}$R$^{17}$), —CH$_2$CN, —CH$_2$F, —CHF$_2$, —CF$_3$, —OCF$_3$, —CH$_2$—CF$_3$, —CF$_2$—CF$_3$, —NO$_2$, —CS—(C$_1$-C$_6$ alkyl), —CS—R$^{18}$, —CS—R$^{19}$, —CS—O—(C$_1$-C$_6$ alkyl), —CS—O—R$^{20}$, —CS—O—R$^{21}$, —CS—N(C$_1$-C$_6$ alkyl)(C$_1$-C$_6$ alkyl), —CS—NR$^{22}$R$^{23}$, —CS—NH$_2$, —CS—N(CR$^{24}$R$^{25}$R$^{26}$)(CR$^{27}$R$^{28}$R$^{29}$), —SO—R$^{30}$, —SO—R$^{31}$, —SO$_2$—R$^{32}$, —SO$_2$—R$^{33}$, —SO—CR$^{34}$R$^{35}$R$^{36}$, —SO—CR$^{37}$R$^{38}$R$^{39}$, —SO$_2$—CR$^{40}$R$^{41}$R$^{42}$, —SO$_2$—CR$^{43}$R$^{44}$R$^{45}$, —SO—N(C$_1$-C$_6$ alkyl)(C$_1$-C$_6$ alkyl), —SO—NR$^{46}$R$^{47}$, —SO—NH$_2$, —SO—N(CR$^{48}$R$^{49}$R$^{50}$)(CR$^{51}$R$^{52}$R$^{53}$), —SO$_2$—N(C$_1$-C$_6$ alkyl)($C_1$-$C_6$ alkyl), —$SO_2$—$NR^{54}R^{55}$, —$SO_2$—$NH_2$, —$SO_2$—$N(CR^{56}R^{57}R^{58})(CR^{59}R^{60}R^{61})$, —$SO_2$—OH, —$SO_2$—$OR^{62}$, —$SO_2$—$CR^{63}R^{64}R^{65}$, —$SO_2$—$OCR^{66}R^{67}R^{68}$, —O—P(O)(OH)$_2$, —O—P(O)($OR^{69}$)($OR^{70}$), —O—P(O)(O—$C_1$-$C_6$ alkyl)(O—$C_1$-$C_6$ alkyl), —P(O)($OR^{71}$)($OR^{72}$), —P(O)(O—$C_1$-$C_6$ alkyl)(O—$C_1$-$C_5$ alkyl), —$CF_2$—P(O)($OR^{73}$)($OR^{74}$), —$CF_2$—P(O)(O—$C_1$-$C_6$ alkyl)(O—$C_1$-$C_6$ alkyl), wherein at least one of the residues $Z^1$, $Z^2$, $Z^3$ is different from hydrogen;

the residues $Z^1$ and $Z^2$ together may also represent a residue —CO—O—CO—$CH_2$—, —CO—O—$CH_2$—$CH_2$—, the residues $Z^2$ and $Z^3$ together may also represent a residue —CO—Z'—$CH_2$—, —CO—O—$CH_2$—, —CO—$CH_2$—$CH_2$—, —CO—O—CO—, —CO—NH—CO— or —Z'—$CH_2$—$CH_2$—, wherein Z' represents one of the following groups: —$CH_2$—, —$CF_2$—, —$C_2H_4$—, —$CF_2$—$CH_2$—, —$CH_2$—$CH_2$—, —O—, —O—$CH_2$—, —NH— or —NH—$CH_2$—;

Q and Q' independently of each other represent a side chain residue of a natural amino acid; or Q together with X' forms a propylenyl residue; or Q' together with X" forms a propylenyl residue;

Y represents a hydroxy group, amino group, $C_1$-$C_6$ alkylamino group, $C_1$-$C_6$ dialkylamino group, $C_1$-$C_6$ alkoxy group, $C_6$-$C_{19}$ aryloxy group, $C_1$-$C_6$ alkyl group, $C_1$-$C_6$ halogenalkyl group, $C_3$-$C_{10}$ heteroaryl group or a $C_6$-$C_{15}$ aryl group; or Y represents a peptide residue of up to 6 amino acids and bound via an amide bond, the C-terminal carbonyl function of which peptide residue carries a hydroxy group, amino group, $C_1$-$C_6$ alkylamino group, $C_1$-$C_6$ dialkylamino group, $C_1$-$C_6$ alkoxy group, $C_1$-$C_6$ alkyl group, $C_1$-$C_6$ halogenalkyl group, $C_3$-$C_{10}$ heteroaryl group or a $C_6$-$C_{15}$ aryl group; or Y represents a peptidomimetic residue of up to 60 carbon atoms and X" represents hydrogen or a $C_1$-$C_6$ alkyl group; and —NXX' is an amino group, $C_1$-$C_{10}$ alkylamino group, $C_6$-$C_{12}$ aralkyloxycarbonyl amino group, $C_1$-$C_{10}$ dialkylamino group, $C_2$-$C_6$ nitrogen heterocycle or a $C_3$-$C_5$ nitrogen heteroaryl group; or the group —NXX' is part of a peptidomimetic residue of up to 60 carbon atoms or X' represents hydrogen or a $C_1$-$C_6$ alkyl group; and X represents a peptide residue of up to 6 amino acids and bound via an amide bond, the N-terminus of which peptide residue carries an amino group, $C_1$-$C_{10}$ alkylamino group, $C_1$-$C_8$-alkyloxycarbonylamino group $C_6$-$C_{12}$ aralkyloxycarbonyl amino group, $C_1$-$C_{10}$ dialkylamino group, $C_2$-$C_6$ nitrogen heterocycle or a $C_3$-$C_5$ nitrogen heteroaryl group;

wherein any of the $C_1$-$C_6$ alkoxy groups, $C_1$-$C_6$ alkyl groups, $C_1$-$C_{10}$ alkylamino groups, $C_1$-$C_8$-alkyloxycarbonylamino groups, $C_6$-$C_{12}$ aralkyloxycarbonyl amino group, $C_1$-$C_{10}$ dialkylamino groups, $C_2$-$C_6$ nitrogen heterocycles as well as $C_3$-$C_5$-nitrogen heteroaryl groups can be independently substituted with up to 5 residues selected from $R^{80}$, $R^{81}$, $R^{82}$, $R^{83}$, $R^{84}$, wherein the residues $R^1$-$R^{84}$ have the meanings as disclosed in WO 2008055488 A1 and stereoisomeric forms, E/Z isomers, enantiomers, enantiomeric mixtures, diastereomers, diastereomeric mixtures, racemates, tautomers, anomers, keto-enol forms, betaine forms, prodrugs, solvates, hydrates as well as pharmacologically acceptable salts of the aforementioned compounds.

The above-mentioned Michael acceptor inhibitors, their synthesis and use are explicitly described in WO 2008055488 A1. It is especially referred to pages 3 to 38 of WO 2008055488 A1.

Furthermore, the present invention describes the production of TG2 in a stabilized open form preferably by the use of the irreversible inhibitors disclosed above. TG2 was produced by recombinant DNA-technology in *Escherichia coli* and purified to homogeneity. Subsequently it was brought to reaction for instance with Z-PIMen(OEt)-QPL-OMe which is the compound $N^\alpha$-benzyloxycarbonyl-{[(E)-(L)-6-amino-hept-2-ene-dicarboxylic acid]-1-ethanoyl}-L-glutaminyl-L-prolinyl-L-leucine methyl ester (compound 2) synthesized in our labs according to the procedure described in WO 2008055488 A1 on page 68; compound 2). By a further purification step excess Z-PIMen(OEt)-QPL-OMe was separated. The resulting TG2-Z-PIMen(OEt)-QPL-OMe-adduct was crystallized. X-ray-structure analysis proved that TG2 is present in its open form after reaction with Z-PIMen(OEt)-QPL-OMe.

Surprisingly it was found that TGs or antigenically active fragments of TGs stabilized by inhibitors and preferably irreversible inhibitors such as the inhibitors disclosed above are present in their open form which is much more sensitive in regard to the detection of autoantibodies against TGs or antigenically active fragments of TGs than the TGs in their closed form or the antigenically active fragments of the TGs in their closed form.

Another aspect of the present invention relates to the use of a gluten-derived peptide with a thiol reactive group or preferably with a Michael acceptor residue as an inhibitor for the production of the open form transglutaminase. Such an adduct of a TG and a gluten-derived peptide is again preferably prepared by reacting the TG with a reactive group such as a Michael acceptor moiety of the gluten-derived peptide. Such an adduct of a TG such as TG2 with a gluten-derived peptide is useful for the simultaneous detection of anti-gliadin antibodies and anti open form transglutaminase autoantibodies.

Consequently the present invention also relates to the use of a gluten-derived peptide with a thiol reactive residue or a Michael acceptor residue as an inhibitor for the production of the open form of a TG such as TG2, wherein the open form TG is useful for the simultaneous detection of anti-gliadin antibodies and anti open form TG2 autoantibodies.

A further aspect of the present invention is directed to immobilized open form TGs which are immobilized on, for instance, titer plates, microtiter plates or well plates. In addition the present invention relates to titer plates, microtiter plates or well plates with immobilized open form TGs and/or immobilized antigenically active fragments of open form TGs on their surface and especially within the wells where the detection reaction is performed.

We found that the stabilized open form or inhibited TG2 can be used for coating of microtiter plates. Sera from blood donors and from celiac disease patients have been subsequently analysed for autoantibodies against the open form TG2 in comparison to commonly used closed form TG2. Surprisingly the sera revealed higher titers for open form TG2 which resulted in a more significant value. In addition some sera could be proofed positive for autoantibodies to open form TG2 which have been diagnosed negative using the closed form TG2 as antigen.

A further aspect of the present invention is directed to a kit for the diagnosis of an autoimmune disorder characterized by the presence of autoantibodies reacting with at least one open form transglutaminase. Such a kit for diagnosis of an autoimmune disorder comprises at least one open form transglutaminase or at least one antigenically active fragment of an open form transglutaminase for the detection of the presence of autoantibodies specific for the open form transglutaminase or the antigenically active fragment of the open form transglutaminase.

These kits can present the open form transglutaminase or antigenically active fragments thereof in a form suitable for use in, for example, the following methods: EIA/ELISA, LiA, FiA, RIA, IRMA, IEMA/EIA, ILMA, IFMA, immunodiffusion, Western-blot, Dot-blot, immunohistochemistry, protein chips or protein arrays.

Such kits may also comprise titer plates, microtiter plates or well plates with open form transglutaminase or antigenically active fragments of the open form transglutaminase immobilized on the surface of the plate.

One smart way to manufacture titer plates, microtiter plates or well plates with open form transglutaminase or antigenically active fragments of the open form transglutaminase immobilized on the surface of the plate is to use the interaction of biotin and biotin binding compounds, like avidin or strepavidin. Therefore biotinlyation of the open form transglutaminase or the antigenically active fragments of the open form transglutaminase is achieved by enzymatic or chemical methods and the biotinylated products are bound to surfaces coated with biotin binding compounds. Another possibility is to bind a biotinylated inhibitor to the TG or antigenically active TG fragment in order to obtain open form TG containing the covalently bound biotinylated inhibitor. Said adduct can be immobilized on the surface of titer plates, microtiter plates or well plates by interacting with biotin binding compounds. Consequently another aspect of the present invention is related to the use of a biotinylated inhibitor for the production of open form transglutaminase for site specific immobilization to surfaces coated with biotin binding compounds.

The above-described kits may further comprise a biotinylated open form transglutaminase or a biotinylated antigenically active open form TG fragment for immobilizing the biotinylated open form transglutaminase or biotinylated antigenically active open form TG fragment to a surface coated with biotin binding compounds. Alternatively the above-described kits may further comprise an open form transglutaminase or an antigenically active fragment thereof reacted with a biotinylated inhibitor for immobilizing the open form transglutaminase biotinylated inhibitor product or the antigenically active fragment biotinylated inhibitor product to a surface coated with biotin binding compounds.

Another aspect of the present invention is directed to the production of open form transglutaminase using an inhibitor linked to one or more antigens specific for autoantibodies not against TG found in patients suffering from autoimmune diseases. An example would be linking the autoantigen in Goodpasture's disease, (noncollagenous-1 (NC1) domain of type IV collagen via the inhibitor to the TG2. Such a construct would allow testing one patient sample for the presence of two or more autoantigenes against different proteins simultaneously.

The most important aspect of the present invention is that the present invention provides novel antigens for autoimmune diagnostics which yield higher and more significant titers resulting in a better diagnostic sensitivity. Furthermore, the present invention shows that the conformation has an impact on triggering the autoimmune disease and accordingly to detect early stage disease states.

Moreover the invention implicates that not tissue transglutaminase but the covalent adduct between transglutaminase and (irreversibly) bound substrate or inhibitor displays the disease state and correlates to inflammation and villous atrophy.

The open form or inhibited transglutaminase is used for the isolation of specific antibodies from patient-derived samples, including blood purification (apheresis).

Thus, the present invention also relates to a method for purifying blood, wherein the open form transglutaminase or antigenically active fragments of the open form transglutaminase are used for binding and removing autoantibodies specific for the open form transglutaminase or antigenically active fragments of the open form transglutaminase from the blood. Such a method uses the common dialysis process. The adsorber material used in the extracorporeal adsorber column contains immobilized open form transglutaminase or antigenically active fragments of the open form transglutaminase in order to bind the autoantibodies against the TG or the antigenically active fragment of the TG or the open form transglutaminase or against the antigenically active fragment of the open form transglutaminase thus removing these autoantibodies from the blood.

Consequently open-form specific antibodies are used for therapeutic approaches, where active and therefore open form transglutaminase shall be neutralized, whereas inactive and therefore closed form transglutaminase shall not be affected.

The open form transglutaminase or inhibited transglutaminase stabilized in its open form is used for the detection of open form specific autoantibodies in samples from body fluids, excretions or tissues. The open form transglutaminase or the antigenically active open form TG fragment is used for a more sensitive and more accurate detection of autoimmune diseases and autoimmune disorders.

Preferably the autoimmune disorder is a food protein sensitivity disorder. Further preferably the autoimmune disorder is a cereal protein sensitivity disorder. Further preferably the cereal protein disorder is a gluten sensitivity disorder with or without enteropathy. Most preferably the gluten sensitivity disorder is selected from the group consisting of or comprising celiac disease, dermatitis herpetiformis, Morbus Duhring and gluten sensitive ataxia.

Further preferably the autoimmune disorder is a paraneoplastic neurological syndrome.

Preferably the autoimmune disorder is a neurological disorder or is characterized by neurological dysfunction. Preferably the autoimmune disorder characterised by neurological dysfunction is anxiety, depression, brainstem encephalitis, cerebral vasculitis, chorea, dementia, epilepsy, cerebral calcifications, headache with white matter abnormalities, neuromyotonia, myasthenia gravis, myopathy, neuropathy, a paraneoplastic syndrome, progressive multifocal leu koencephalopathy, progressive myoclonic encephalopathy, multiple sclerosis, chronic inflammatory demyelinating polyneuropathy, schizophreniform disorder or stiff-person syndrome.

Most preferably the autoimmune disorder characterised by neurological dysfunction is immune mediated ataxia, encephalitis, cerebral vasculitis, neuromyotonia, myasthenia gravis, polymyositis, immune mediated peripheral neuropathy, a paraneoplastic syndrome, multiple sclerosis, chronic inflammatory demyelinating polyneuropathy, headache with white matter abnormalities, epilepsy with occipital cerebral calcifications, or stiff-person syndrome.

Preferably the autoimmune disorder is a gluten sensitivity disorder with neurological symptoms selected from the group consisting of or comprising: cerebellar ataxia, neuropathy, myopathy, ataxia with myoclonus, myelopathy, cerebral calcifications, headache with white matter abnormalities, dementia, chorea or Stiff-person syndrome.

Preferably the autoimmune disorder characterised by neurological dysfunction is ataxia, ataxia with myoclonus, encephalitis, polymyositis, epilepsy with occipital cerebral calcifications, loss of sensation or muscle weakness.

Preferably the paraneoplastic neurological syndrome is paraneoplastic cerebellar degeneration, paraneoplastic encephalomyelitis, paraneoplastic opsoclonus-myoclonus, cancer associated retinopathy, paraneoplastic stiff-person syndrome, paraneoplastic necrotizing myelopathy, a motor neuron syndrome including amyotrophic lateral sclerosis (ALS) and subacute motor neuronopathy, subacute sensory neuronopathy, polyradiculoneuropathy (Guillain-Barré), brachial neuritis or neuromyotonia.

Preferably the autoimmune disorder is an endocrinologic autoimmune disease. Preferably the endocrinologic autoimmune disease is selected from the group consisting of or comprising: diabetes mellitus type 1, Addisons disease and Hashimoto's thyroiditis.

Preferably the autoimmune disorder is a dermatologic autoimmune disease. Preferably the dermatologic autoimmune disease is selected from the group consisting of or comprising: psoriasis and dermatitis herpetiformis.

Preferably the autoimmune disorder is a gastrointestinal autoimmune disease. Preferably the gastrointestinal autoimmune disease is selected from the group consisting of or comprising: celiac disease, pernicious anaemia and ulcerative colitis.

Preferably the open form TG2 is used for the detection auf autoantibodies in the sera of patients suffering from autoimmune diseases characterized by the presence of autoantibodies against open form TG2. Moreover the open form TG2 is preferably used for the detection of autoantibodies in samples from patients suffering from a gluten sensitive disorder, especially suffering from celiac disease. A preferred embodiment of the present invention is directed to the use of open form TG2 for the detection of specific autoantibodies in celiac disease patients who have no or low antibody titers against closed form TG2.

In another embodiment of the present invention the open form TG2 is used for the detection of autoantibodies in patients suffering from diabetes mellitus type 1 and in a still further embodiment of the present invention the open form TG2 is used for the detection of specific autoantibodies in recent onset celiac disease patients which did not develop antibodies against closed form TG2 yet.

Preferably the open form TG3 is used for the detection auf autoantibodies in the sera of patients suffering from autoimmune diseases characterized by the presence of autoantibodies against open form TG3. Moreover the open form TG3 is preferably used for the detection of autoantibodies in samples from patients suffering from dermatitis herpetiformis.

Preferably the open form TG6 is used for the detection auf autoantibodies in the sera of patients suffering from autoimmune diseases characterized by the presence of autoantibodies against open form TG6. Moreover the open form TG6 is preferably used for the detection of autoantibodies in samples from patients suffering from neuropathy, ataxia or gluten sensitive ataxia or stiff person syndrom.

In the present invention any method and device suitable for the diagnostic detection of proteins or antibodies in samples of body fluids or in tissue samples can be used to detect autoantibodies reacting with open form transglutaminases. Examples of such methods and devices include: EIA/ELISA, LiA, FiA, RIA, IRMA, IEMA/EIA, ILMA, IFMA, immunodiffusion, Western-blot, Dot-blot, immunohistochemistry, protein chips or protein arrays. Thus another aspect of the present invention is directed to protein chips and protein arrays containing at least one open form transglutaminase or at least one antigenically active open form TG fragment preferably in an immobilized form. Such chips and arrays may preferably contain more than one open form transglutaminase isoform selected from transglutaminase 1, transglutaminase 2, transglutaminase 3, transglutaminase 4, transglutaminase 5, transglutaminase 6, transglutaminase 7, or coagulation factor XIII, preferably in an immobilized form.

Another aspect of the present invention relates to pharmaceutical formulations and pharmaceutical compositions containing the open form of a TG together with at least one pharmaceutically acceptable carrier, excipient, solvent and/or diluents.

The preferred preparations and formulations are in administrable form which is suitable for oral application or injection. These administrable forms include pills, tablets, film tablets, coated tablets, capsules, solutions, dispersions and deposits.

For example, for oral administration in the form of tablets or capsules, the open form TG may be combined with any oral nontoxic pharmaceutically acceptable inert carrier, such as lactose, starch, sucrose, cellulose, magnesium stearate, dicalcium phosphate, calcium sulfate, talc, mannitol, ethyl alcohol (liquid forms) and the like. Moreover, when desired or needed, suitable binders, lubricants, disintegrating agents and colouring agents may also be incorporated in the mixture.

Suitable binders include starch, gelatine, natural sugars, corn sweeteners, natural and synthetic gums such as acacia, sodium alginate, carboxymethyl-cellulose, polyethylene glycol and waxes. Among the lubricants that may be mentioned for use in these dosage forms are boric acid, sodium benzoate, sodium acetate, sodium chloride, and the like. Disintegrants include starch, methylcellulose, guar gum and the like. Sweetening and flavouring agents and preservatives may also be included where appropriate. Some of the terms noted above, namely disintegrants, diluents, lubricants, binders and the like, are discussed in more detail below.

Additionally, the compositions of the present invention may be formulated in sustained release form to provide a controlled release of the open form TG. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

Liquid form preparations include solutions, suspensions and emulsions especially for injection. As an example may be mentioned water or water-propylene glycol solutions for parenteral injections or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier such as inert compressed gas, e.g. nitrogen.

For preparing suppositories, a low melting wax such as a mixture of fatty acid glycerides such as cocoa butter is first melted, and the active ingredient is dispersed homogeneously therein by stirring or similar mixing. The molten homogeneous mixture is then poured into convenient sized molds, allowed to cool and thereby solidifies.

Also included are solid form preparations which are intended to be converted, shortly before use, to liquid form preparations for either oral or parenteral administration. Such liquid forms include solutions, suspensions and emulsions especially for injection.

The term capsule refers to a special container or enclosure made of methyl cellulose, polyvinyl alcohols, or denatured gelatines or starch for holding or containing compositions comprising the active ingredients. Hard shell capsules are typically made of blends of relatively high gel strength bone and pork skin gelatines. The capsule itself may contain small amounts of dyes, opaquing agents, plasticizers and preservatives.

Tablet means compressed or molded solid dosage form containing the active ingredients with suitable diluents. The tablet can be prepared by compression of mixtures or granulations obtained by wet granulation, dry granulation or by compaction well known to a person skilled in the art.

Oral gels refers to the active ingredients dispersed or solubilized in a hydrophilic semi-solid matrix.

Another aspect of the present invention relates to the open form of a TG or to pharmaceutical formulations and pharmaceutical compositions containing the open form of a TG for the use in medicine.

These pharmaceutical preparations may preferably be used for a hyposensitisation therapy for patients suffering from autoimmune diseases caused by a gluten intolerance. Consequently, another aspect of the present invention is directed to the use of an open form of a TG, such as TG2, for the preparation of a pharmaceutical composition for hyposensitisation of a patient suffering from an autoimmune disorder caused by a gluten intolerance.

As used herein, the term "hyposensitisation therapy" refers to an immunologic desensitization or allergen-specific immunotherapy, wherein a patient is vaccinated with initially low doses of an open form TG such as TG1, TG2, TG3, TG4, TG5, TG6, TG7 or coagulation factor XIII, which are increased during the treatment period with the aim of inducing immunologic tolerance.

Accordingly the present invention discloses a method for hyposensitizing a mammal including a human by administering a pharmaceutically effective amount of an open form TG to said mammal which suffered from an autoimmune disorder caused by gluten intolerance. The open form or inhibited TG is preferably administered starting from low doses with increasing doses during the treatment period after a gluten free diet of the patient and at a time where the patient does not show any symptoms of the autoimmune disease which could be measured clinically or by biopsy or serology.

DETAILED DESCRIPTION OF THE PREFERRED EMBODIMENTS

Example 1

Production of Stabilized Open Form TG2

Figure 1:
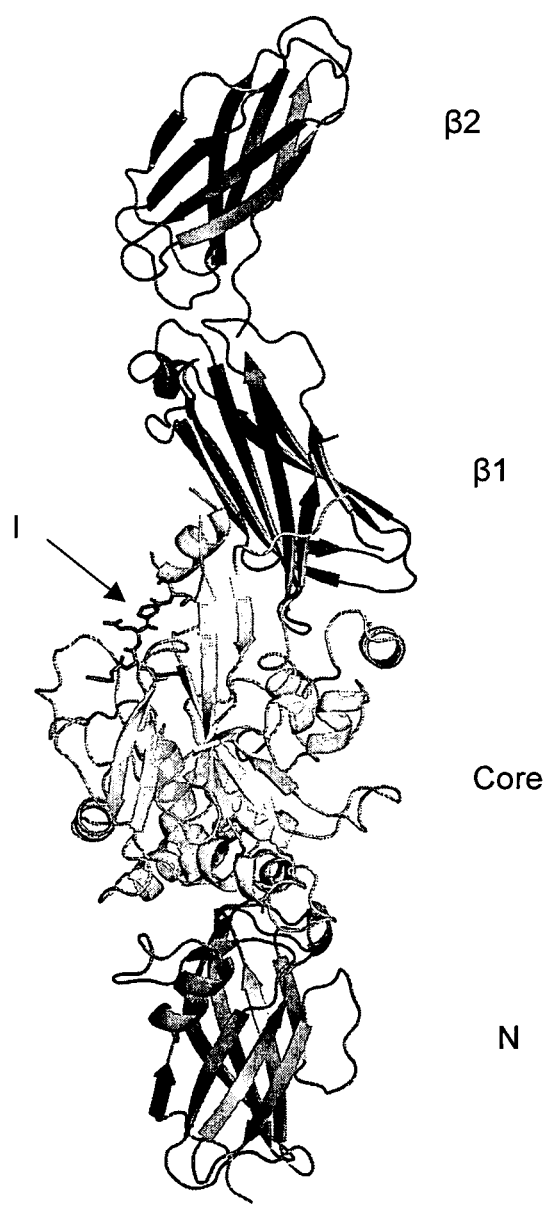
FIG. 1 shows the structure of TG2-Z-PIMen(OEt)-QPL-OMe-conjugate revealing the open conformation of TG2. N: N-terminal fibroncetin binding domain; Core: catalytic core domain; β1 and β2: beta sheet domains; I: Inhibitor (Z-PIMen(OEt)-QPL-OMe)

*Escherichia coli* cells producing recombinant TG2 were centrifuged at 3,700 rpm for 20 minutes. The pellet was resuspended in buffer and lysed by high pressure homogenization. After centrifugation, the supernatant was applied to a column containing Ni-NTA resin (Qiagen, Hilden, Germany). The column was rinsed with buffer until baseline was reached. TG2 was then eluted in a buffer containing 300 mM imidazole. Fractions containing TG2 were pooled and further purified by anion exchange and gel permeation chromatography. Preparation of stabilized open form TG2 for crystallization was performed by incubating freshly prepared TG2 with Z-PIMen(OEt)-QPL-OMe (inhibitor) at a ratio of 1 to 50 at room temperature for 30 min and then at 4° C. overnight. Excess inhibitor was removed by anion exchange chromatography. TG2-inhibitor conjugate was concentrated to 8 mg/mL. Glycerol was added to a final concentration of 10%. Storage was performed at −80° C.

Example 2

Crystallization and Verification of the Open Form

Crystallization has been performed applying the sitting-drop vapor diffusion method and 1.75-2.25 M $(NH_4)_2SO_4$, 100 mM HEPES pH 6.75-7.5 at 18° C. Rhombic-shaped crystals appeared in 5 to 7 days (Space group: $P4_12_12$; Unit cell constants: a, b=71.0 Å, c=310.4 Å). The data set was collected with synchrotron radiation and yielded a resolution of 2.5 Å. Processing of the data allowed to determine the position of the inhibitor in the TG2 and confirmed the open conformation.

Example 3

Coating of Microtiter-Plates with Open Form TG2

Open form or inhibited TG2 has been produced as described in example 1. Nunc Lockwell Maxisorp plates have been coated overnight at 4° C. with 100 μl per well coating solution, composed of 20 mM Tris-HCL, pH 7.4, 150 mM NaCl and 1 μg/ml open form TG2. Then coating solution was removed and plates were washed intensively with TBS (20 mMTris-HCl, pH7.4, 150 mM NaCl) containing 0.01% Tween 20. Blocking was performed by the addition of 200 μl TBS containing 3% bovine serum albumin for 1 h. Blocking solution was removed and plates were washed intensively with TBS (20 mMTris-HCl, pH7.4, 150 mM NaCl) containing 0.01% Tween 20.

Example 4

Analysis of Sera

Sera from celiac disease patients and from blood donors have been analysed for antibodies against closed form TG2 and open form TG2 by Enzyme Linked Immuno Sorbent Assays (ELISA). For the detection of IgA-type autoantibodies against closed form TG2 ELISA-Kit E001 from Zedira GmbH, Darmstadt, Germany was used, whereas for IgG-type autoantibodies kit E002 from Zedira GmbH, Darmstadt, Germany was used.

For detection of IgA and IgG-type antibodies against open conformation TG2 the microtiter-plates as described in example 3 have been used. All other components necessary for performing the ELISAs have been taken from Zedira kits E001 and E002 respectively. Accordingly the protocols of E001 and E002 have been used: 10 μl of each serum have been diluted with 990 μl sample buffer, mixed thoroughly and centrifuged to sediment insoluble particles. Immediately prior to use, the solid phase was washed once with 350 μL wash buffer per well. After 10 seconds the wash butter was completely removed. 100 μL of the calibrators, the negative and positive control and the diluted samples have rapidly been dispensed into the micro plate wells. After incubation for 30 minutes at room temperature the wells have been washed 4 times with 350 μl wash buffer. Using an 8-channel pipette 100 μl of conjugate have been dispensed per well subsequently and incubated for 30 min. After a further washing procedure 100 μl substrate solution have been dispensed into the wells and incubated for 30 minutes. Then 100 μl stop solution have been added. Finally the plates were agitated on an orbital shaker for about 10 seconds and the absorbance at 450 nm has been determined.

Results are given in Tab. 1-4. Surprisingly the standards (mixture of celiac disease patients sera) yielded significantly higher extinction values at 450 nm when the open form TG2 was used as antigen in the IgG-ELISAs (Tab. 1 and 2). This demonstrates a higher titer of antibodies to open form TG2 in the standards than to closed form TG2. Blood donor's serum 26, which is tested positive in the closed form ELISA is clearly negative in the open form ELISA. Therefore the open form TG2-ELISA provides less false positive results in autoimmune diagnostics (Tab. 2).

TABLE 1 anti-IgG-ELISAs using standard TG2 (closed form) and the novel open form TG2 on blood donors sera. Positive values are written in bold letters.

| | anti-IgG ELISAs | | | |
|---|---|---|---|---|
| | Closed form TG2 | | Open form TG2 | |
| blood donors | ΔE450 nm [mOD] | U/mL (Cutoff: 3 U/ml) | ΔE450 nm [mOD] | U/mL (Cutoff: 3 U/ml) |
| Standard 1 | 43 | 0 | 47 | 0 |
| Standard 2 | 162 | 1 | 327 | 1 |
| Standard 3 | 376 | 3 | 733 | 3 |
| Standard 4 | 817 | 10 | 1492 | 10 |
| Standard 5 | 1429 | 30 | 2283 | 30 |
| Standard 6 | 2038 | 100 | 2716 | 100 |
| Serum No | | | | |
| 1 | 137 | 0.79 | 237 | 0.66 |
| 2 | 131 | 0.74 | 174 | 0.44 |
| 3 | 132 | 0.74 | 192 | 0.50 |
| 4 | 148 | 0.88 | 217 | 0.59 |
| 5 | 150 | 0.90 | 239 | 0.67 |
| 6 | 137 | 0.79 | 189 | 0.49 |
| 7 | 112 | 0.58 | 188 | 0.49 |
| 8 | 155 | 0.94 | 222 | 0.61 |
| 9 | 125 | 0.69 | 200 | 0.53 |
| 10 | 97 | 0.45 | 147 | 0.35 |
| 11 | 168 | 1.05 | 190 | 0.50 |
| 12 | 184 | 1.19 | 264 | 0.76 |
| 13 | 154 | 0.93 | 160 | 0.39 |
| 14 | 162 | 1.00 | 219 | 0.60 |
| 15 | 161 | 0.99 | 259 | 0.74 |
| 16 | 252 | 1.80 | 300 | 0.90 |
| 17 | 142 | 0.83 | 201 | 0.53 |
| 18 | 166 | 1.03 | 241 | 0.68 |
| 19 | 130 | 0.73 | 202 | 0.54 |
| 20 | 123 | 0.67 | 164 | 0.40 |
| 21 | 136 | 0.78 | 234 | 0.65 |
| 22 | 171 | 1.08 | 251 | 0.71 |
| 23 | 163 | 1.01 | 238 | 0.67 |
| 24 | 115 | 0.60 | 191 | 0.50 |
| 25 | 143 | 0.84 | 226 | 0.62 |
| 26 | 535 | 4.89 | 380 | 1.21 |
| 27 | 125 | 0.69 | 188 | 0.49 |
| 28 | 161 | 0.99 | 235 | 0.66 |
| 29 | 214 | 1.45 | 296 | 0.88 |
| 30 | 198 | 1.31 | 276 | 0.81 |
| 31 | 183 | 1.18 | 227 | 0.63 |
| 32 | 144 | 0.85 | 214 | 0.58 |
| 33 | 96 | 0.44 | 146 | 0.34 |
| 34 | 151 | 0.91 | 228 | 0.63 |
| 35 | 151 | 0.91 | 241 | 0.68 |
| 36 | 130 | 0.73 | 183 | 0.47 |
| 37 | 140 | 0.81 | 214 | 0.58 |
| 38 | 117 | 0.62 | 170 | 0.43 |
| 39 | 167 | 1.04 | 223 | 0.61 |
| 40 | 168 | 1.05 | 252 | 0.72 |

TABLE 2 anti-IgG-ELISAs using standard TG2 (closed form) and the novel open form TG2 on celiac disease patients sera. Positive values are written in bold letters.

| | anti-IgG ELISAs | | | |
|---|---|---|---|---|
| | Closed form TG2 | | Open form TG2 | |
| Patients sera | ΔE450 nm [mOD] | U/mL (Cutoff: 3 U/ml) | ΔE450 nm [mOD] | U/mL (Cutoff: 3 U/ml) |
| Standard 1 | 44 | 0 | 51 | 0 |
| Standard 2 | 161 | 1 | 351 | 1 |
| Standard 3 | 363 | 3 | 763 | 3 |
| Standard 4 | 833 | 10 | 1530 | 10 |
| Standard 5 | 1440 | 30 | 2327 | 30 |
| Standard 6 | 1969 | 100 | 2755 | 100 |
| Serum No | | | | |
| 41 | 201 | 1.36 | 519 | 1.69 |
| 42 | 109 | 0.55 | 159 | 0.35 |
| 43 | 154 | 0.94 | 204 | 0.49 |
| 44 | 176 | 1.14 | 233 | 0.59 |
| 45 | 142 | 0.84 | 461 | 1.44 |
| 46 | 119 | 0.63 | 281 | 0.75 |
| 47 | 112 | 0.57 | 186 | 0.43 |
| 48 | 148 | 0.89 | 284 | 0.76 |
| 49 | 110 | 0.56 | 165 | 0.36 |
| 50 | 700 | 7.57 | 1427 | 8.68 |
| 51 | 976 | 13.09 | 1716 | 12.74 |
| 52 | 130 | 0.73 | 231 | 0.58 |
| 53 | 128 | 0.72 | 462 | 1.44 |
| 54 | 143 | 0.84 | 200 | 0.48 |
| 55 | 90 | 0.39 | 135 | 0.27 |
| 56 | 116 | 0.61 | 164 | 0.36 |
| 57 | 107 | 0.53 | 117 | 0.21 |
| 58 | 88 | 0.37 | 105 | 0.17 |
| 59 | 79 | 0.30 | 92 | 0.13 |

TABLE 2-continued anti-IgG-ELISAs using standard TG2 (closed form) and the novel open form TG2 on celiac disease patients sera. Positive values are written in bold letters.

| | anti-IgG ELISAs | | | |
|---|---|---|---|---|
| | Closed form TG2 | | Open form TG2 | |
| Patients sera | ΔE450 nm [mOD] | U/mL (Cutoff: 3 U/ml) | ΔE450 nm [mOD] | U/mL (Cutoff: 3 U/ml) |
| 60 | 97 | 0.45 | 172 | 0.39 |
| 61 | 100 | 0.47 | 144 | 0.30 |
| 62 | 104 | 0.51 | 139 | 0.28 |
| 63 | 99 | 0.47 | 134 | 0.26 |
| 64 | 102 | 0.49 | 121 | 0.22 |
| 65 | 115 | 0.60 | 129 | 0.25 |
| 66 | 144 | 0.85 | 228 | 0.57 |
| 67 | 559 | 5.43 | 1355 | 7.84 |
| 68 | 365 | 2.98 | 673 | 2.47 |
| 69 | 263 | 1.96 | 795 | 3.20 |
| 70 | 152 | 0.92 | 246 | 0.63 |
| 71 | 90 | 0.39 | 166 | 0.37 |
| 72 | 300 | 2.33 | 325 | 0.91 |
| 73 | 235 | 1.68 | 455 | 1.41 |
| 74 | 89 | 0.38 | 172 | 0.39 |
| 75 | 133 | 0.75 | 385 | 1.13 |
| 76 | 77 | 0.28 | 161 | 0.35 |
| 77 | 115 | 0.60 | 171 | 0.38 |
| 78 | 219 | 1.54 | 302 | 0.83 |
| 79 | 331 | 2.66 | 1093 | 5.34 |
| 80 | 107 | 0.54 | 133 | 0.26 |

Detection of autoantibodies of the IgG-type in patient's sera (Tab. 2) revealed lower mUnit-values in the majority of all sera which were tested negative, enlarging the distance to the cutoff. Sera 50, 51 and 67 have been positive in the closed and open form TG2, but the titers for the open form again have been proved higher for two sera. Whereas Serum 68 was positive in the closed form and negative in the open form ELISA, sera 69 and 79 could be proved positive with the open form ELISA.

In Summary use of open form TG2 as antigen in celiac disease IgG-diagnostics results in a higher diagnostic specificity and sensitivity than closed form TG2.

The results of the IgA-type autoantibody-detection are presented in Tab. 3 (blood donor's sera). Whereas the closed form TG2-ELISA could detect 1 positive serum (26), open form TG2 detected 5 positive sera (4, 17, 25, 26, 27).

From 3 negative patients sera using closed form TG2, 1 could be detected positive using the open form TG2, thus increasing the diagnostic sensitivity (Tab. 4).

With two exceptions higher Unit-values have been measured in patient's sera using the open form TG2. Several patients' sera like 49, 71, 76 or 80 showed more than 100% higher titers in the open form assay. This shows that patients have autoantibodies specific to the open conformation of TG2. Especially when the titers are close to the cut off the open form TG2 yields more reliable diagnostic results (e.g. sera 61 and 70).

The analysis-results of further patients sera are described in the following:

The patient number A is a child, diagnosed for celiac disease by histology upon biopsy. While negative or doubtful results are obtained using standard diagnostics (2.0 U/ml for IgG and 1.2 U/ml for IgA, cut off=3 U/ml), the novel antigen is able to detect early antibodies. (13 U/ml for IgG and 45 U/ml for IgA)

Patient number B and C presented to the doctor with severe symptoms of celiac disease confirmed by biopsy. However, only comparable low or doubtful titers against TG2 (2.9 or 3.5 U/ml, cutoff=3 U/ml) have been found. Indeed, the new antigen shows tremendously higher titers correlating with severity of the inflammation and villous atrophy (Patient B, Marsh II by biopsy: 19 U/ml, Patient C, Marsh III by biopsy: 39 U/ml).

Patient D was diagnosed with diabetes type one. While the standard ELISA displays no antibodies against TG2 the novel antigen could detect IgG (11 U/ml) as well as IgA (46 U/ml) antibodies.

Patient E was diagnosed for psoriasis. Whereas no TG2-autoantibodies could be detected with the standard ELISA, clearly positive values (IgA: 37 U/ml, IgG: 21 U/ml) have been obtained using the open form TG2 as antigen in the ELISA.

In conclusion we have shown the presence of autoantibodies of the IgA and the IgG-type which specifically recognize the open conformation TG2. Usage of open form TG2 increases diagnostic sensitivity and specificity in the corresponding autoimmune diagnostics, e.g. celiac disease diagnostics.

Therefore with the newly developed open form TG2 we provide a novel diagnostic antigen which helps to improve TG2-based diagnostics. It may be used in all methods used for the detection of antibodies in samples of body fluids or tissue samples. Examples for such methods include: EIA/ELISA, LiA, FiA, RIA, IRMA, IEMA/EIA, ILMA, IFMA, immunodiffusion, Western-blot or Dot-blot. Any of these methods could be adapted for diagnostic purposes using the antigen described herein in detail by a person skilled in the art.

As transglutaminases are structurally related, the phenomenon surprisingly found for TG2 and described in detail in this application, will also be applicable to other transglutaminases like TG3 in the diagnosis of dermatitis herpetiformis or TG6 in the diagnosis of gluten sensitive neurological disorders.

TABLE 3 anti-IgA-ELISAs using standard TG2 (closed form) and the novel open form TG2 on healthy donors sera. Positive values are written in bold letters.

| | anti-IgA ELISAs | | | |
|---|---|---|---|---|
| | Closed form TG2 | | Open form TG2 | |
| Blood donors sera | ΔE450 nm [mOD] | U/mL (Cutoff: 3 U/ml) | ΔE450 nm [mOD] | U/mL (Cutoff: 3 U/ml) |
| Standard 1 | 45 | 0 | 45 | 0 |
| Standard 2 | 101 | 1 | 108 | 1 |
| Standard 3 | 209 | 3 | 220 | 3 |
| Standard 4 | 537 | 10 | 568 | 10 |
| Standard 5 | 1161 | 30 | 1264 | 30 |
| Standard 6 | 2185 | 100 | 2322 | 100 |
| Serum No | | | | |
| 1 | 86 | 0.73 | 120 | 1.20 |
| 2 | 84 | 0.70 | 106 | 0.97 |
| 3 | 137 | 1.65 | 177 | 2.20 |
| 4 | 148 | 1.86 | 251 | 3.59 |
| 5 | 80 | 0.62 | 110 | 1.03 |
| 6 | 97 | 0.93 | 172 | 2.11 |
| 7 | 104 | 1.05 | 173 | 2.13 |
| 8 | 115 | 1.25 | 198 | 2.59 |
| 9 | 121 | 1.36 | 166 | 2.00 |
| 10 | 57 | 0.21 | 68 | 0.36 |
| 11 | 78 | 0.59 | 106 | 0.97 |
| 12 | 74 | 0.52 | 117 | 1.15 |
| 13 | 118 | 1.31 | 188 | 2.40 |
| 14 | 89 | 0.78 | 115 | 1.12 |
| 15 | 115 | 1.25 | 145 | 1.63 |
| 16 | 81 | 0.64 | 114 | 1.10 |

TABLE 3-continued anti-IgA-ELISAs using standard TG2 (closed form) and the novel open form TG2 on healthy donors sera. Positive values are written in bold letters.

| | anti-IgA ELISAs | | | |
|---|---|---|---|---|
| | Closed form TG2 | | Open form TG2 | |
| Blood donors sera | ΔE450 nm [mOD] | U/mL (Cutoff: 3 U/ml) | ΔE450 nm [mOD] | U/mL (Cutoff: 3 U/ml) |
| 17 | 128 | 1.49 | 252 | 3.60 |
| 18 | 84 | 0.70 | 107 | 0.98 |
| 19 | 90 | 0.80 | 136 | 1.47 |
| 20 | 70 | 0.45 | 87 | 0.66 |
| 21 | 88 | 0.77 | 168 | 2.04 |
| 22 | 85 | 0.71 | 140 | 1.54 |
| 23 | 87 | 0.75 | 105 | 0.95 |
| 24 | 57 | 0.21 | 72 | 0.42 |
| 25 | 147 | 1.84 | 513 | 8.81 |
| 26 | 212 | 3.06 | 559 | 9.80 |
| 27 | 118 | 1.31 | 226 | 3.11 |
| 28 | 91 | 0.82 | 155 | 1.81 |
| 29 | 121 | 1.36 | 178 | 2.22 |
| 30 | 103 | 1.04 | 160 | 1.89 |
| 31 | 97 | 0.93 | 133 | 1.42 |
| 32 | 71 | 0.46 | 98 | 0.84 |
| 33 | 89 | 0.78 | 113 | 1.08 |
| 34 | 76 | 0.55 | 95 | 0.79 |
| 35 | 100 | 0.98 | 154 | 1.79 |
| 36 | 71 | 0.46 | 76 | 0.49 |
| 37 | 84 | 0.70 | 127 | 1.32 |
| 38 | 62 | 0.30 | 85 | 0.63 |
| 39 | 74 | 0.52 | 117 | 1.15 |
| 40 | 81 | 0.64 | 122 | 1.23 |

TABLE 4 anti-IgA-ELISAs using standard TG2 (closed form) and the novel open form TG2 on celiac disease patients sera. Positive values are written in bold letters.

| | anti-IgA ELISAs | | | |
|---|---|---|---|---|
| | Closed form TG2 | | Open form TG2 | |
| Celiac disease patients sera | ΔE450 nm [mOD] | U/mL (Cutoff: 3 U/ml) | ΔE450 nm [mOD] | U/mL (Cutoff: 3 U/ml) |
| Standard 1 | 45 | 0 | 45 | 0 |
| Standard 2 | 101 | 1 | 108 | 1 |
| Standard 3 | 209 | 3 | 220 | 3 |
| Standard 4 | 537 | 10 | 568 | 10 |
| Standard 5 | 1161 | 30 | 1264 | 30 |
| Standard 6 | 2185 | 100 | 2322 | 100 |
| Serum No | | | | |
| 41 | 262 | 4.00 | 363 | 5.78 |
| 42 | 299 | 4.75 | 479 | 8.09 |
| 43 | 350 | 5.80 | 457 | 7.64 |
| 44 | 579 | 11.22 | 829 | 16.31 |
| 45 | 509 | 9.44 | 690 | 12.73 |
| 46 | 724 | 15.16 | 1160 | 27.02 |
| 47 | 821 | 18.07 | 1041 | 22.76 |
| 48 | 1889 | 72.59 | 2326 | 105.61 |
| 49 | 1174 | 30.91 | 2132 | 86.06 |
| 50 | 1464 | 44.42 | 2050 | 78.51 |
| 51 | 1617 | 53.08 | 2169 | 89.71 |
| 52 | 1865 | 70.57 | 2346 | 107.65 |
| 53 | 1911 | 74.43 | 2487 | 122.04 |
| 54 | 1297 | 36.27 | 1804 | 59.31 |
| 55 | 351 | 5.82 | 431 | 7.12 |
| 56 | 474 | 8.61 | 693 | 12.80 |
| 57 | 414 | 7.21 | 644 | 11.66 |
| 58 | 346 | 5.72 | 542 | 9.39 |
| 59 | 277 | 4.30 | 437 | 7.24 |
| 60 | 87 | 0.79 | 111 | 1.14 |
| 61 | 308 | 4.92 | 501 | 8.53 |
| 62 | 326 | 5.31 | 532 | 9.18 |
| 63 | 193 | 2.70 | 306 | 4.70 |
| 64 | 362 | 6.07 | 570 | 10.00 |
| 65 | 373 | 6.30 | 588 | 10.38 |
| 66 | 83 | 0.71 | 128 | 1.45 |
| 67 | 1665 | 56.14 | 2270 | 99.85 |
| 68 | 3176 | 201.73 | 3354 | 210.44 |
| 69 | 1975 | 79.95 | 2340 | 107.04 |
| 70 | 246 | 3.69 | 360 | 5.74 |
| 71 | 505 | 9.36 | 1261 | 31.03 |
| 72 | 1356 | 39.00 | 1506 | 42.09 |
| 73 | 1372 | 39.78 | 1808 | 59.60 |
| 74 | 409 | 7.10 | 632 | 11.37 |
| 75 | 2126 | 94.57 | 2751 | 148.92 |
| 76 | 309 | 4.95 | 678 | 12.46 |
| 77 | 604 | 11.86 | 898 | 18.26 |
| 78 | 2208 | 102.96 | 2595 | 133.01 |
| 79 | 2365 | 118.98 | 2830 | 157.03 |
| 80 | 284 | 4.45 | 610 | 10.88 |

Example 5

Hyposensitisation of a Patient

Patient F suffered from celiac disease and has been on gluten free diet for 8 years. According to biopsy and serology Patient F was on remission and showed no celiac disease symptoms any more. Patient F has been injected subcutaneously a solution containing open TG2, which has been produced according to example 1. Injections have been repeated weekly over a period of six months; the doses have been increased over this period in order to reach the maintenance dose. The application has then been repeated applying the maintenance dose once a month for 1.5 years. Patient F was kept on a strict gluten free diet for this whole hyposensitisation therapy period. Later-on the patient started to consume minor amounts (1 g per day) of gluten in addition to the gluten free diet. No celiac disease symptoms could be measured clinically or by biopsy or serology.

Example 5 demonstrates that the open form of a TG can be used for a hyposensitisation therapy for patients suffering from autoimmune diseases caused by a gluten intolerance.

Example 6

Analysis of Sera

Further Sera have been analyzed according to the protocol outlined in Example 4. Patients groups 1-5 are defined by a positive celiac disease diagnosis, but a low or negative titer for TG2 autoantibodies as measured by classical assays using closed TG2 as antigen.

Figure 2:
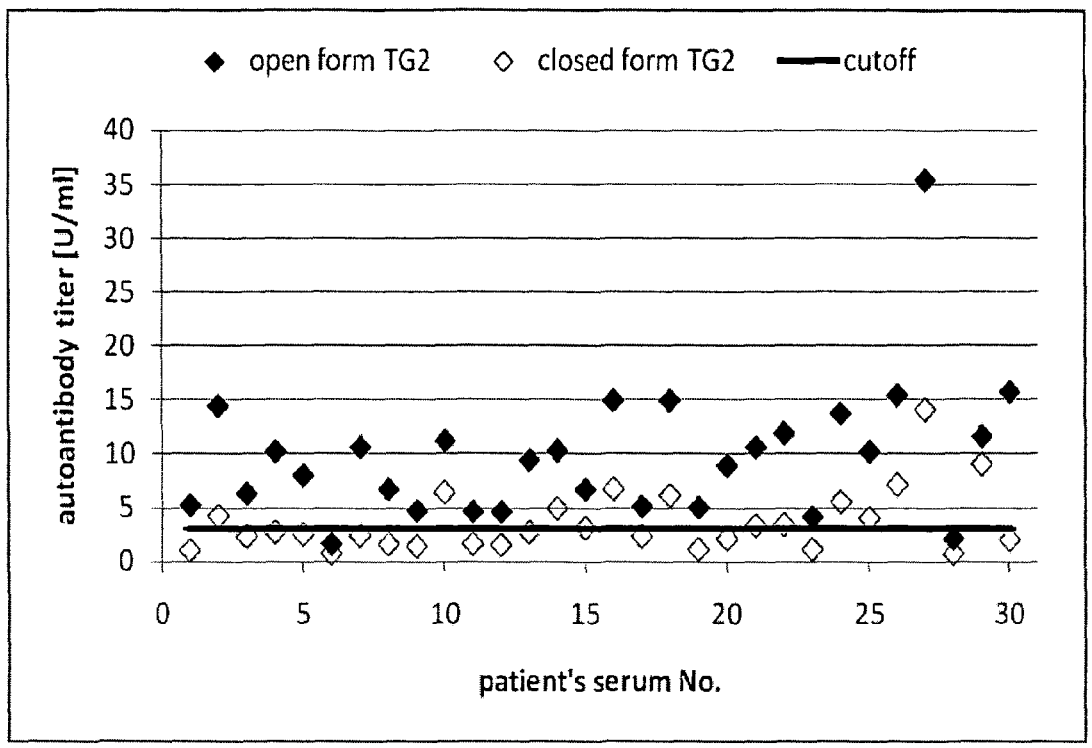
FIG. 2 IgA-type autoantibody titer in sera from patients with overt small bowel mucosal villous atrophy FIG. 3 IgA-type autoantibody titer in sera from patients with early stage celiac disease FIG. 4 IgA-type autoantibody titer in sera from patients with unresponsive treated celiac disease FIG. 5 IgA-type autoantibody titer in sera from patients with overt small bowel mucosal villous atrophy and for one year on gluten free diet.

Group 1 is defined by overt small bowel mucosal villous atrophy. 30 sera of this kind have been analyzed. In general the autoantibody titer measured with the open form TG2 was higher than that measured for the closed form TG2. 14 sera were slightly positive in the closed form TG2 IgA-ELISA, whereas in the open form TG2 IgA-ELISA 28 sera could be detected positive, as shown in FIG. 2. Thus 93% of patients could be detected serologically using the open form TG2 as antigen, whereas only 47% could be detected with the closed form TG2. Therefore the open form TG2 is able to detect the majority of celiac disease patients which is not the case for the closed form TG2. In the IgG ELISA no positive sera could be detected using the closed form TG2 as antigen, whereas 5 sera have been detected as positive using the open form TG2. This shows, that open form TG2 is also able to detect more IgG-type autoantibodies than closed form TG2 and thus is able to detect more celiac disease patients by ELISA-based serology.

Figure 3:
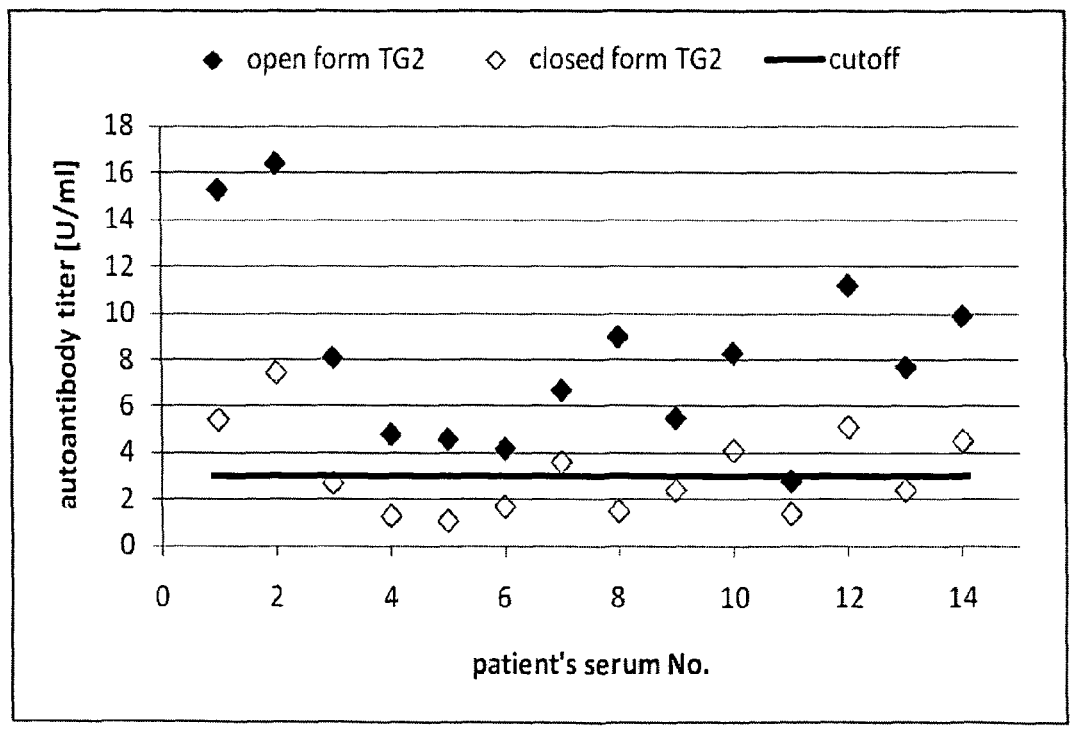

Group 2 is defined by early stage celiac disease characterized by mild enteropathy. 14 sera have been analyzed. Again the titers are generally higher for the open form TG2. 6 sera (42%) have been positive for IgA-type autoantibodies against closed TG2 whereas 13 (93%) revealed to be positive using the open form TG2 as antigen (FIG. 3). Thus also in the group of early stage celiac disease the open form TG2 is able to detect the majority of celiac disease patients by serology which again is not the case for closed form TG2.

Figure 4:
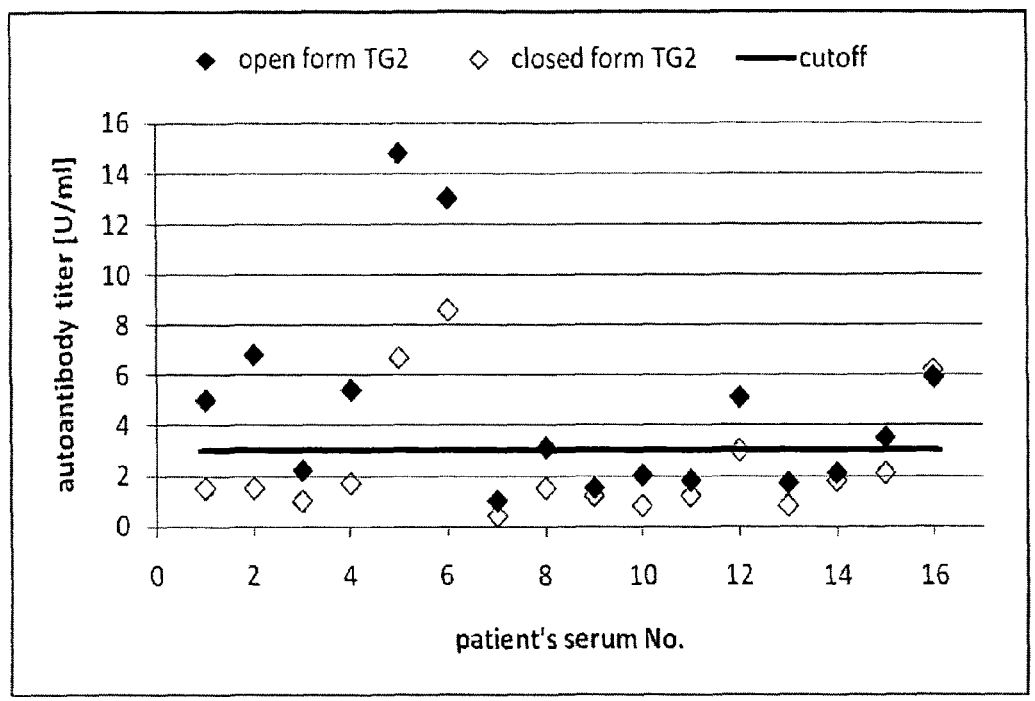

Group 3 is defined by unresponsive treated celiac disease. 16 patients have been analyzed. Again the titers are generally higher for the open form TG2. 3 (19%) sera have been positive for the closed form TG2-ELISA (IgA), whereas 9 (56%) have been positive using the open form TG2 as antigen (FIG. 4). Therefore the open form TG2 is able to detect about three times more celiac disease patients by serology in this group.

Figure 5:
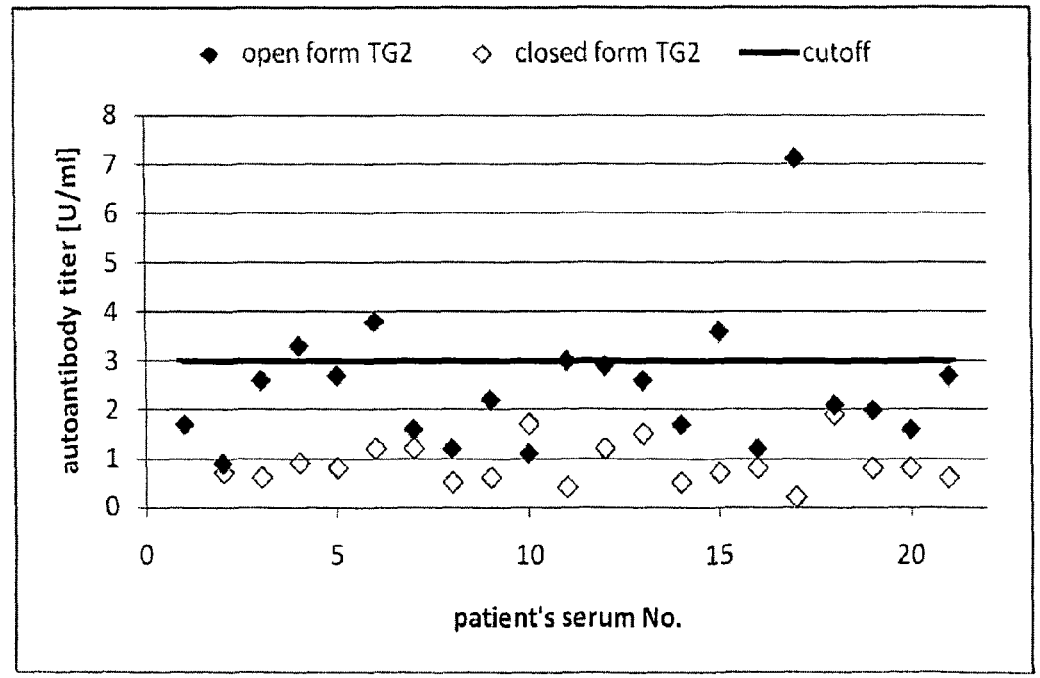

Group 4 is defined by overt small bowel mucosal villous atrophy and for one year on gluten free diet. Using the closed form TG2-ELISA all 21 patients did not show TG2-autoantibodies anymore. Testing the sera with the open form TG2-ELISA proved that in 5 patients (24%) TG2-autoantibodies are still present (FIG. 5). Therefore open TG2 is able to detect even minor amounts of TG2-autoantibodies and helps to detect celiac disease patients where gluten free diet is not completely successful.

Figure 6:
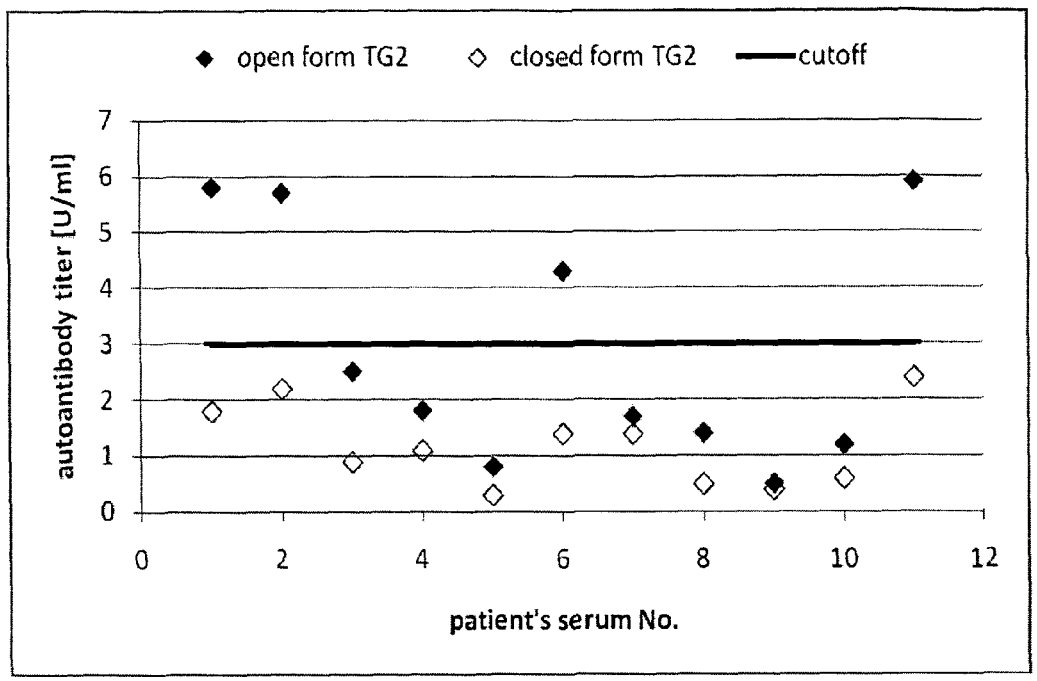
FIG. 6 IgA-type autoantibody titer in sera from early stage Celiac disease-patients after one year on gluten free diet FIG. 7 IgA-type autoantibody titer in sera from patients where celiac disease has been suspected, but so far could not be diagnosed by the celiac disease diagnostic methods available.

Group 5 is defined by early stage CD-patients after one year on gluten free diet. The closed form showed successful diet for all of the 11 patients (no TG2-autoantibodies anymore), whereas the open form showed for 4 patients that TG2-autoantibodies are still present (FIG. 6), indicating that the diet has not been completely successful.

Figure 7:
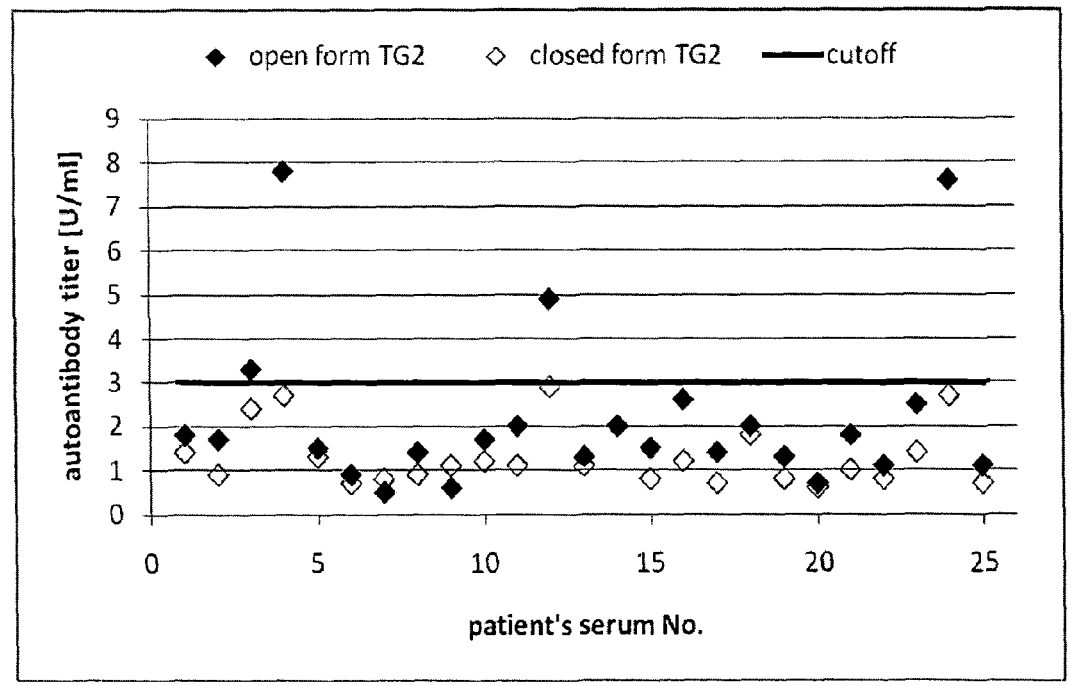

Group 6 is defined by patients where celiac disease has been suspected, but so far could not be diagnosed by the celiac disease diagnostic methods available. 4 out of the 25 sera tested where positive using the open form TG2 (FIG. 7). Thus these 4 patients could be detected as celiac disease patients.

Figure 8:
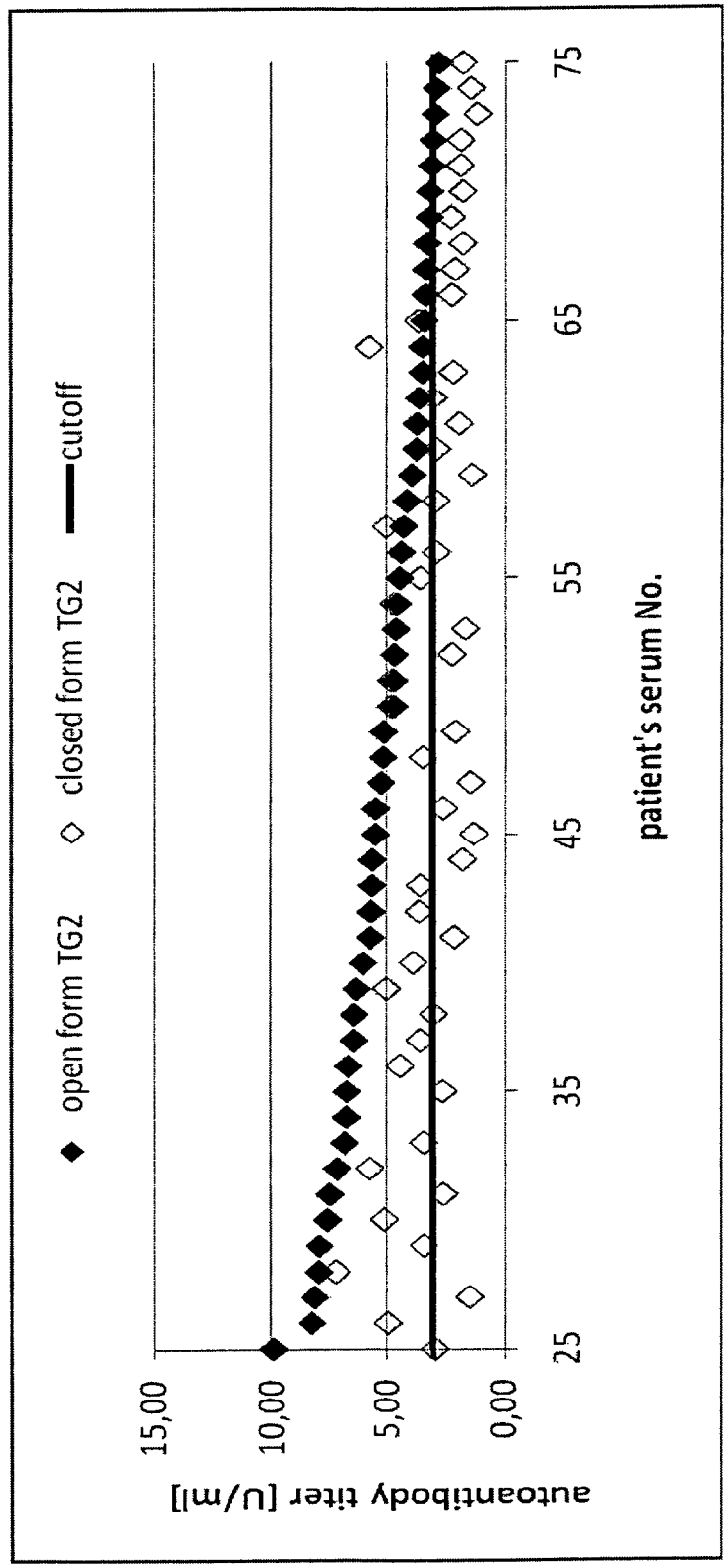
FIG. 8: IgA-type autoantibody titer in sera from patients on gluten free diet. 50 samples described in the text with titers close to the cut off are shown. The sera have been sorted according to the open form titer.

Group 7 is a cohort of 150 non-selected celiac disease patients on gluten free diet. 52 sera (35%) revealed to be positive in the closed-form TG2-IgA-ELISA, whereas 71 (48%) have been positive in the open form IgA-ELISA. FIG. 8 shows the data of the most interesting cases close to the cut off, where most closed from TG2-ELISA results are negative. Therefore open TG2-based diagnostics revealed, that not one third, but half of the patients still have TG2-autoantibodies indicating that they did not follow a successful diet.

Example 7

Construction of Open Form TG2 Using Further Inhibitors

Open from TG2 has been prepared according to example 1 but using the following inhibitors:
A. Z-PIMen(OEt)-QPL-OMe (inhibitor described in example 1)
B. Boc-(6-diazo-5-oxonorleucinyl)-QIV-OMe
C. Z-Pimen(OMe)-V-tetrahydroindolizine-OMe
D. Ac-LGPG-(DON)-SLVIG-OMe
E. 1,3,4,5-Tetramethyl-2[(2-oxopropyl)thio]imidazolium chloride A is a Michael-acceptor based inhibitor with a peptidic backbone. B also has a peptidic backbone, but diazo-5-oxonorleucin (or "DON") as reactive group. C is a Michael-acceptor with a peptidomimetic backbone. Whereas A and B have gluten-derived backbones, D has a casein and therefore non-gluten derived sequence. E is a non-peptidic, non-peptidomimetic molecule alkylating the active site cystein of transglutaminase.

Microtiterplates have then been coated with the respective open conformation TG2 variants according to example 3. 10 celiac disease patients sera have been analyzed according to example 4 for IgA-type auto-antibodies with plates coated with closed form TG2, and open form TG2 variants prepared using the inhibitors A, B, C, D and E.

The results given in the following table show that the signal obtained is independent from the inhibitor used for preparation of the stabilized open conformation TG2. It can also be seen that the open form TG2 yields higher titers and can help to diagnose patients which have a negative titer in the closed TG2-assay (sera PS148 and PSE1).

TABLE 5 anti-IgA-ELISAs using standard TG2 (closed form) and the novel open form TG2 (derived using different inhibitors) on celiac disease patients sera. Positive values are written in bold letters

| | | Open form TG2 variants | | | | |
|---|---|---|---|---|---|---|
| Serum | TG2 [U/ml] | A [U/ml] | B [U/ml] | C [U/ml] | D [U/ml] | E [U/ml] |
| cut off | 3 | 3 | 3 | 3 | 3 | 3 |
| PS148 | 2 | 4 | 4 | 5 | 4 | 3 |
| PS149 | 100 | 100 | 100 | 100 | 100 | 100 |
| PS150 | 14 | 68 | 70 | 65 | 72 | 74 |
| PS151 | 17 | 24 | 28 | 23 | 22 | 25 |
| PS152 | 6 | 19 | 22 | 22 | 18 | 19 |
| PS153 | 33 | 55 | 55 | 60 | 54 | 49 |
| PS154 | 9 | 33 | 30 | 30 | 34 | 37 |
| PS155 | 100 | 100 | 100 | 100 | 100 | 100 |
| PS158 | 5 | 18 | 20 | 17 | 17 | 17 |
| PSE1 | 1 | 9 | 10 | 9 | 9 | 10 |

Example 8

Preparation of Biotinylated Open Conformation TG2 and Detection of Autoantibodies in Celiac Disease Patient's Sera TG2 prepared according to example 1 has been biotinylated by incubating 4 mg TG2 (in a 2.4 mg/ml-solution in PBS) with 20 fold molar excess of Sulfo-NHS-Biotin at 20° C. for 30 min. Excess of Sulfo-NHS-Biotin was removed using a desalting column. The degree of labeling was determined to 1.7 Biotin molecules per TG2 (HABA-Assay, Pierce). In a second step biotinylated TG2 was used for the preparation of open conformation biotinylated TG2, as described in example 3. Coating of streptavidin coated microtiterplates (Pierce) was performed according to the manufacturer's protocol.

5 blood donors sera (DS) and 5 patient's sera (PS) have been analyzed for IgA-type autoantibodies using the above mentioned plates coated with biotinylated open TG2. The results are presented in the table below. Production of biotinylated open conformation TG2 and subsequent immobilization on streptavidin coated solid phase clearly allows the detection of autoantibodies in celiac disease patient's sera.

TABLE 6 anti-IgA-ELISAs using the biotinylated open form TG2 on healthy donors and celiac disease patients' sera.
Positive values are written in bold letters.

| Serum | biotinylated open TG2 - autoantibodies (IgA) mOD$_{450}$ |
|---|---|
| DS1 | 110 |
| DS2 | 153 |
| DS3 | 98 |
| DS4 | 178 |
| DS5 | 140 |
| PS148 | 201 |
| PS149 | 2546 |
| PS150 | 405 |
| PS151 | 432 |
| PS152 | 289 |

The results given in table 6 show that the auto-antibody titers obtained for the patient's sera are generally much higher than for the blood donors sera. The data correlates to the signals obtained in example 7. Therefore it can be seen that the biotinylated open form TG2 yields comparable titers and can also help to diagnose patients which have a negative titer in the closed TG2-assay.

Example 9

Preparation of Open Form TG3, Open Form TG6 and Detection of Autoantibodies in Patient's Sera Dispase-activated TG3 (Zedira product No. T124) and TG6 (Zedira product No. T121) were incubated with Z-PI-Men(OEt)-QPL-OMe according to example 1. Microtiterplates have been coated with the reaction product according to example 3. Sera from patients suffering from celiac disease (CD), gluten ataxia (GA), gluten ataxia with enteropathy (GAE), stiff man syndrome (SMS), Genetic ataxia (GenA), idiopathic sporadic ataxia (ISA) and dermatitis herpetiformis (DH) have been analyzed for autoantibodies against TG3 (Zedira Kit, product No. E009), TG6 (Zedira Kits, product No. E003 and E004) and with the respective open conformation antigens as described above. For the TG3 variants IgA-type auto-antibodies have been determined, whereas for the TG6 variants IgA and IgG-type autoantibodies where measured. The results are summarized in the table below.

TABLE 7 anti-IgA/IgG-ELISAs using the novel open form TG3 and the novel open form TG6 on different patients' sera. Positive values are written in bold letters

| serum | diagnosis | TG3 IgA [U/ml] | open form TG3 IgA [U/ml] | TG6 IgA [U/ml] | TG6 IgG [U/ml] | open form TG6 IgA [U/ml] | open form TG6 IgG [U/ml] |
|---|---|---|---|---|---|---|---|
| | cutoff | 3 | 3 | 16 | 30 | 40 | 60 |
| PS6 | CD | 24 | 24 | 69 | 45 | 291 | 92 |
| PS7 | GA | 4 | 4 | 14 | 9 | 88 | 47 |
| PS8 | CD | 2 | 2 | 10 | 17 | 50 | 119 |
| PS9 | CD | 1 | 2 | 10 | 19 | 41 | 34 |
| PS10 | GAE | 1 | 2 | 10 | 11 | 44 | 34 |
| PS11 | SMS | 4 | 4 | 13 | 5 | 72 | 34 |
| PS29 | GA | nd | nd | 18 | 8 | 73 | 33 |
| PS30 | GA | 1 | 2 | 6 | 23 | 24 | 54 |
| PS31 | GA | 2 | 3 | 12 | 22 | 74 | 36 |
| PS32 | GAE | 3 | 7 | 29 | 22 | 193 | 63 |
| PS33 | CD | nd | nd | 31 | 20 | 82 | 72 |
| PS34 | CD | nd | nd | 37 | 33 | 105 | 72 |
| PS35 | GAE | 16 | 34 | 100 | 17 | 300 | 61 |
| PS36 | GAE | 1 | 1 | 6 | 54 | nd | nd |
| PS37 | GA | 1 | 1 | 5 | 100 | 27 | 296 |
| PS38 | GA | 3 | 3 | 17 | 12 | 74 | 45 |
| PS39 | GenA | 0 | 1 | 4 | 13 | 13 | 41 |
| PS40 | GenA | 1 | 1 | 7 | 11 | 27 | 35 |
| PS41 | GenA | 0 | 0 | 4 | 43 | 21 | 86 |
| PS42 | GenA | 0 | 1 | 4 | 6 | 15 | 34 |
| PS43 | GenA | 0 | 1 | 7 | 13 | 27 | 32 |
| PS44 | CD | 16 | 17 | 18 | 100 | 46 | 236 |
| PS45 | CD | 0 | 0 | 4 | 22 | 24 | 174 |
| PS46 | GA | 1 | 1 | 45 | 8 | 100 | 46 |
| PS47 | ISA | 1 | 0 | 64 | 9 | 135 | 34 |
| PS48 | DH | 12 | 11 | 8 | 13 | 44 | 63 |
| PS49 | DH | 70 | 70 | 4 | 11 | 29 | 54 |
| PS50 | DH | 29 | 28 | 18 | 12 | 55 | 29 |
| PS51 | DH | 5 | 6 | 4 | 11 | 25 | 60 |
| PS52 | DH | 17 | 21 | 6 | 9 | 28 | 33 |
| PS53 | DH | 20 | 20 | 13 | 14 | 45 | 58 |
| PS54 | DH | 0 | 0 | 3 | 8 | 11 | 43 |
| PS55 | DH | 37 | 29 | 5 | 8 | 40 | 40 |
| PS56 | DH | 4 | 3 | 3 | 15 | 24 | 54 |
| PS57 | DH | 7 | 6 | 4 | 8 | 25 | 38 |
| PS58 | DH | 1 | 1 | 59 | 14 | 235 | 71 |

The sera generally show comparable titers for closed TG3 as well as open form TG3 auto-antibodies. There are 4 sera with a significant difference. Serum PS31 is negative (2 U/ml) for the closed form TG3 but positive for the open form (3 U/ml). Serum PS32 (7 U/ml) is clearly above the cut off for anti-open form TG3, whereas the titer for the closed form is on the cut-off level. Serum PS35 has twice the titer for open form TG3 autoantibodies than for TG3-autoantibodies. Both titers are clearly positive. Serum PS55 has a 30% higher titer for the closed form but is clearly positive for both TG3-antigens. Therefore in some sera having negative or low titers for autoantibodies against closed TG3 the usage of the open conformation TG3 as antigen can reveal more clearly positive titers.

With respect to TG6, the auto-antibody titers are generally much higher for the open form than for the closed form, independently from the Ig-type. Further 8 sera negative for TG6 show positive titers for open conformation TG6 in the IgA-ELISA. The same is true for 7 sera in the IgG-ELISA.

Therefore using TG6 in its open conformation helps to reveal auto-antibodies in the serum of patients which cannot be detected with the closed form as antigen.

In addition the data show, that PS11 (serum taken from a patient suffering from stiff man syndrome) is positive for the open conformation TG6-titer (IgA-type). Positive open TG6-titers can also be found in patients suffering from celiac disease, gluten ataxia with enteropathy, gluten ataxia and dermatitis herpetiformis.

Example 10

Analysis of Sera From Patients Suffering from Various Disorders Using ELISA-Kits with TG2 or TG6 in Their Open and Their Closed Conformation ELISA-kits with the antigens TG2 (closed and open conformation) or TG6 (closed and open conformation have been prepared according to the above mentioned examples and sera form patients suffering from various disorders have been analyzed for autoantibodies against the respective antigens.

Patients suffered from the following disorders: Addisons disease (AD, chronic adrenal insufficiency, characterized by antibodies against corticosteroid producing cells of the adrenal glands); autoimmune hepatitis (AH); chronic inflammatory demyelinating polyneuropathy (CIDP, loss of the myelin sheath of the peripheral nerves); Hashimoto's thyroiditis (HT, hypothyroidism, characterized by autoantibodies against thyroid peroxidase or thyroglobulin); rheumatoid arthritis (RA, arthritis characterized by auto-antibodies attacking especially joint lining and cartilage; multiple sclerosis (MS); Polymyositis (PM, inflammatory myopathy); ulcerative colitis (UC); diabetes mellitus type 1 (DM1, characterized by autoantibodies against beta cells); epilepsy (EP); neuropathy (NE).

In the mentioned examples it could be shown, that autoantibodies are present and generally the titer for the antigens in the open conformation are higher. Especially in cases with a low titer, positive or negative, but close to the cutoff, the open conformation antigens are beneficial for diagnostic purposes. The data are given in the following table.

TABLE 8

Analysis for various patient's sera for autoantibodies against the closed and open conformations of TG3 and TG6. Positive titers are written in bold letters.

| | | TG2 | open form TG2 | TG6 | | open form TG6 | |
|---|---|---|---|---|---|---|---|
| | | IgA [U/ml] | IgA [U/ml] | IgA [U/ml] | IgG [U/ml] | IgA [U/ml] | IgG [U/ml] |
| serum | cutoff disorder | 3 | 3 | 16 | 30 | 40 | 60 |
| PS210 | AD | 1 | 6 | nd | nd | nd | nd |
| PS223 | AH | 2 | 8 | nd | nd | nd | nd |
| PS225 | CIDP | 2 | 15 | 4 | 0 | 78 | 34 |
| PS214 | HT | 1 | 2 | 11 | 45 | 32 | 124 |
| PS215 | HT | 1 | 0 | 15 | 66 | 53 | 153 |
| PS254 | MS | 1 | 2 | 23 | 20 | 69 | 37 |
| PS256 | MS | 1 | 0 | 15 | 23 | 77 | 45 |
| PS257 | MS | 0 | 0 | 12 | 25 | 31 | 69 |
| PS261 | PM | 2 | 5 | nd | nd | nd | nd |
| PS265 | UC | 0 | 3 | nd | nd | nd | nd |
| PS266 | UC | 1 | 14 | nd | nd | nd | nd |
| PS267 | UC | 1 | 9 | nd | nd | nd | nd |
| PS268 | UC | 2 | 7 | nd | nd | nd | nd |
| PS211 | DM1 | 3 | 9 | nd | nd | nd | nd |
| PS212 | DM1 | 1 | 12 | nd | nd | nd | nd |
| PS213 | DM1 | 2 | 4 | nd | nd | nd | nd |
| PS209 | EP | 0 | 1 | 2 | 19 | 12 | 61 |
| PS271 | EP | 1 | 1 | 17 | 27 | 55 | 72 |
| PS272 | EP | 0 | 0 | 14 | 17 | 61 | 55 |
| PS233 | NE | 1 | 3 | 15 | 22 | 36 | 73 |

Example 11

Analysis of Sera from Patients Suffering from Celiac Disease or Gluten Ataxia Using ELISA-Kits with TG2 or TG6 Fragments in Their Open and Their Closed Conformation Tissue transglutaminase fragments were produced recombinantly in *E. coli* as deletion mutants lacking C-terminal amino acids from positions S538 and E447 according to example 1 an methods known to persons skilled in the art. The resulting truncated tissue transglutaminases still were enzymatically active, although the activity was reduced to 5 and 1% respectively compared to the full length enzyme. Transglutaminase 6 fragment lacking the C-terminal amino acids from position G594 was produced accordingly.

Inhibition with Z-PIMen(OEt)-QPL-OMe was performed according to example 1 but at room temperature over night to generate the open form transglutaminase fragments. Microtiterplates have been coated with the open form transglutaminase-fragments according to example 3. Sera of celiac disease patients and gluten ataxia patients have been analyzed. The data given in tab. 9 demonstrate that also the open transglutaminase fragments show higher autoantibody-titers compared to the closed full length form.

TABLE 9 analysis of celiac disease (CD) patient's sera for autoantibodies (IgA-type) against TG2, Open TG2 and the Open TG2-fragments ΔS538 and ΔE447 and analysis of gluten ataxia (GA) patients sera for autoantibodies against TG6, Open TG6 and Open TG6 fragment ΔG594. Titers are given in U/ml. Positive Titers are written in bold letters.

| Serum | disorder | TG2 | Open TG2 | Open TG2 ΔS538 | Open TG2 ΔE447 | TG6 | Open TG6 | Open TG6 ΔG594 |
|---|---|---|---|---|---|---|---|---|
| cut off |  | 3 | 3 | 3 | 3 | 16 | 40 | 40 |
| PS48 | CD | 2 | 4 | 4 | 3 | nd | nd | nd |
| PS49 | CD | 100 | 100 | 100 | 100 | nd | nd | nd |
| PS50 | CD | 14 | 68 | 60 | 45 | nd | nd | nd |
| PS51 | CD | 17 | 24 | 24 | 19 | nd | nd | nd |
| PS52 | CD | 6 | 19 | 19 | 22 | nd | nd | nd |
| PS53 | CD | 33 | 55 | 59 | 51 | nd | nd | nd |
| PSE1 | CD | 1 | 9 | 9 | 7 | nd | nd | nd |
| PS29 | GA | nd | nd | nd | nd | 18 | 73 | 66 |
| PS30 | GA | nd | nd | nd | nd | 6 | 21 | 28 |
| PS31 | GA | nd | nd | nd | nd | 12 | 74 | 71 |

Example 12

Immobilisation of Open TG on Polysulfone-Absorber

Hollow fibers or particles made of polysulfone are provide with amino groups, as described in J Polym Sci, Part A: Polym Chem 41: 1316-1329, 2003, by a reaction with n-butyllithium provided with benzonitrile and reduction with cyanoborohydride in acidic medium for benzylamine.

The activation of the carboxyl groups of the open form TG2 was made with CME-CDI (N-cyclohexyl-N'-(2-morpholino-ethyl) carbodiimide methyl-p-toluolsulfat). For this purpose a reaction solution of open form TG2 and CME-CDI; 1:1 (w/w) at 4° C.; in 0.1 M MES buffer (2-(N-morpholino) ethane sulfonic acid) prepared at pH 4.75 and stirred for half an hour. The reaction solution is passed for 4 hours at room temperature on the surface of the aminated hollow fibers. The fibers are then washed with PBS buffer and water to neutrality.

A patient was treated with an apheresis system containing the above described absorber.

This patient had been removed blood twice before treatment, with positive values for antibodies against open form TG2 but not for TG2. After the apheresis the signal for open TG2 was reduced below the threshold.

Example 13

Native PAGE Analysis of Transglutaminases and Inhibited Transglutaminases Shows Conformational Differences 2 μg of TG2, open TG2, TG3, dispase activated TG3, inhibited dispase activated TG3, TG6 and inhibited TG6 have been mixed with 3× loading buffer (56 mM Tris-HCl ph6.8, 22.5% glycerol, 11% bromophenylblue) and loaded on a 4-20% gradient gel (BioRad). 25 mm Tris-HCl pH 8.5, 122 mM glycin has been used as electrophoresis buffer. Native PAGE has been run for 75 min and 125 V at 4° C. Coomassie-staining of the gel revealed, that TG2 migrates faster than open TG2, indicating a conformational change which leads to slower migration in the native PAGE and which has already been proven by crystal structure analysis. TG6 and inhibited TG6 showed comparable migration properties than TG2 and open TG2, indicating conformational changes of open TG6 comparable to open TG2.

Dispase activation cleaves TG3 in two polypeptides which do not dissociate. TG3 and dispase activated TG3 migrated both as a single band. Dispase activated TG3 migrates slower than non-activated TG3. Inhibited TG3 migrated in two bands. These results show that inhibition of TG3 enables dissociation of the two subunits, so that hidden or new epitopes become accessible.

Example 14

Detection of Open-TG6-Autoantibodies in Patients' Sera Suffering from Various Disorders Using an ELISA-Technique which Eliminates Unspecific Signals Open TG6 prepared according to example 9 has been used to coat microtiterplates according to example 3. In addition half of the plates has been coated in with coating buffer lacking open TG6 (background control wells: BG-wells). The ELISA-protocol has been modified by measuring each sample twice in open TG6-coated wells and BG-wells. The median value of the BG-wells has been subtracted from the median value of the open TG6 coated wells before calculating the Units. Serum specific background due to non-specific binding to the wells could be eliminated.

The results are given in Tab. 10 and again prove that usage of the open conformation yields more positive titers than the closed conformation. In addition it reduces the number of false positive samples in the IgG-assay (sera GenA8 and GenA16).

TABLE 10

Analysis of healthy donor's (N) and patient's sera for autoantibodies against TG6 and Open TG6 in an assay which eliminates non-specific background. Positive titers are written in bold letters.

| | IgG | | | IgA | |
|---|---|---|---|---|---|
| | TG6 | open TG6 | | TG6 | open TG6 |
| cutoff | 30 | 30 | cutoff | 16 | 57 |
| Healthy Controls | | | Healthy Controls | | |
| N 1 | 4 | 8 | N 1 | 6 | 0 |
| N 3 | 15 | 14 | N 3 | 11 | 56 |
| N 4 | 11 | 22 | N 4 | 5 | 23 |
| N 6 | 23 | 17 | N 6 | 3 | 0 |
| N 8 | 14 | 15 | N 8 | 9 | 42 |
| N 9 | 18 | 19 | N 9 | 6 | 9 |
| N 10 | 18 | 22 | N 10 | 7 | 79 |
| N 12 | 25 | 18 | N 12 | 5 | 30 |
| N 13 | 16 | 25 | N 13 | 8 | 29 |
| N 14 | 19 | 23 | N 14 | 9 | 42 |
| N 15/N 11 | 17 | 13 | N 15/N 11 | 5 | 7 |
| N 17 | 9 | 9 | N 17 | 4 | 14 |
| N 18 | 11 | 10 | N 18 | 6 | 33 |
| N 19 | 12 | 11 | N 19 | 14 | 55 |
| N 20 | 17 | 9 | ratio | 0/14 | 1/14 |
| ratio | 0/15 | 0/15 | | | |
| Genetic Ataxia | | | Genetic Ataxia | | |
| GenA 1 | 27 | 24 | | | |
| GenA 2 | 18 | 14 | GenA 2 | 10 | 3 |
| GenA 3 | 12 | 25 | GenA 3 | 6 | 1 |
| GenA 4 | 13 | 18 | GenA 4 | 4 | 30 |
| GenA 7 | 11 | 10 | GenA 7 | 7 | 21 |
| GenA 8 | 43 | 27 | GenA 8 | 4 | 9 |
| GenA 10 | 6 | 13 | GenA 10 | 4 | 17 |
| GenA 11 | 12 | 15 | GenA 11 | 3 | 49 |
| GenA 12 | 24 | 17 | GenA 12 | 3 | 0 |
| GenA 16 | 33 | 22 | GenA 16 | 17 | 67 |
| GenA 18 | 17 | 15 | GenA 18 | 13 | 53 |
| GenA 20 | 7 | 12 | GenA 20 | 8 | 55 |
| GenA 21 | 9 | 15 | GenA 21 | 3 | 9 |
| ratio | 2/13 | 0/13 | ratio | 1/13 | 1/13 |
| Ataxia and gluten sensitivity | | | Ataxia and gluten sensitivity | | |
| GA 3 | 14 | 30 | GA 3 | 12 | 49 |
| GA 22 | >100 | >100 | GA 22 | 5 | 27 |
| GA 24 | 29 | 44 | GA 25 | 16 | 110 |
| GA 28/MISC 2 | 27 | 33 | GA 26 | 21 | 63 |
| GA 41 | 8 | 20 | GA 38 | 5 | 50 |
| GA 43 | 13 | 30 | GA 41 | 18 | 61 |
| GA 50 | 15 | 31 | GA 43 | 17 | 50 |
| GA 53 | 16 | 18 | GA 49 | 5 | 38 |
| GA/ISA 44 | 12 | 14 | GA 50 | 17 | 152 |
| GA/ISA 46 | 10 | 22 | GA 51 | 6 | 58 |
| GA/ISA 47 | 33 | 89 | GA 53 | 6 | 52 |
| ISA 20 | 9 | 13 | GA/ISA 44 | 4 | 36 |
| ISA 22 | 14 | 17 | ISA 4 | 58 | 88 |
| ISA 34 | 4 | 8 | ISA 9 | 66 | 79 |
| GAe 1 | 18 | 31 | ISA 20 | 58 | 102 |
| GAe 5 | 31 | 26 | ISA 22 | 8 | 43 |
| GAe 19 | 60 | 63 | ISA 29 | 16 | 62 |
| GAe 32 | 25 | 31 | ISA 34 | 6 | 20 |
| GAe 34 | 22 | 11 | GAe 1pg | 51 | 179 |
| GAe 35 | 36 | 15 | GAe 11 | 14 | 137 |
| GAe 49 | 15 | 39 | GAe 17 | 13 | 17 |
| GAe 50 | 8 | 12 | GAe 31 | 11 | 76 |
| GAe 51 | 18 | 19 | GAe 35 | 17 | 39 |
| ratio | 5/23 | 11/23 | GAe 49 | 9 | 39 |
| | | | GAe 51 | 13 | 123 |
| | | | ratio | 10/25 | 13/25 |
| Neuropathy and gluten sensitivity | | | Neuropathy and gluten sensitivity | | |
| GN 1 | 44 | 38 | GN 1 | 16 | 89 |
| GN 9 | 50 | 37 | GN 6 | 38 | 129 |
| GN 15 | 20 | 35 | GN 9 | 46 | 176 |
| GA/GN 18 | 32 | 27 | GN 10 | 18 | 74 |
| GN 21 | 10 | 50 | GN 16 | 22 | 121 |
| GN 23 | 9 | 17 | GN 21 | 17 | 172 |
| GN 19g | >100 | 65 | GN 23 | 5 | 75 |
| ratio | 4/7 | 5/7 | ratio | 7/7 | 7/7 |
| Celiac Disease | | | Celiac Disease | | |
| CD 13 | 67 | 72 | CD 2 | 14 | 42 |
| CD 17 | 25 | 94 | CD 3 | 34 | 29 |
| CD 22 | 18 | 33 | CD 10 | 11 | 90 |
| ratio | 1/3 | 2/3 | CD 13 | 90 | 103 |
| | | | CD 17 | 12 | 32 |
| | | | CD 18 | 10 | 67 |
| | | | CD 22 | 15 | 49 |
| | | | CD/WMA 4 | 14 | 154 |
| | | | ratio | 2/8 | 4/8 |

Gen A: genetic ataxia;
GA: gluten ataxia;
MISC: miscellaneous;
ISA: idiopathic sporadic ataxia;
GAe: gluten ataxia with enteropathy;
GN: gluten neuropathy;
CD: celiac disease;
WMA: white matter abnormality.
The ratio of positives are given below each patient's group.

The invention claimed is:

1. Method for the diagnosis of an autoimmune disorder, comprising:
   providing a sample from a subject suspected of having the autoimmune disorder;
   contacting the sample with an open form transglutaminase using the open form transglutaminase or antigenically active fragments of the open form transglutaminase;
   determining if autoantibodies from the sample bind to the open form transglutaminase or antigenically active fragments of the open form transglutaminase, wherein binding of autoantibodies in the sample indicate that the subject has the autoimmune disorder; and
   wherein the autoimmune disorder is selected from the group consisting of Addisons's disease, autoimmune hepatitis, chronic inflammatory demyelinating polyneuropathy, Hashimoto thyroiditis, multiple sclerosis, polymyositis, ulcerative colitis, psoriasis, gluten sensitive disorders, celiac disease, dermatitis herpetiformis, diabetes mellitus type 1, dementia, epilepsy, headache with white matter abnormalities, neuropathy, gluten ataxia, idiopathic sporadic ataxia, ataxia with enteropathy, and stiff-man syndrome.

2. Method according to claim 1, wherein the open form transglutaminase or the antigenically active fragment of the open form transglutaminase is selected from TG1, TG2, TG3, TG4, TG5, TG6, TG7 or coagulation factor XIII or antigenically active fragments of TG1, TG2, TG3, TG4, TG5, TG6, TG7 or coagulation factor XIII.

3. Method according to claim 1, wherein the open form transglutaminase or the antigenically active fragment of the open form transglutaminase is obtained by reacting the not open form transglutaminase or the antigenically active fragment of the not open form transglutaminase with an inhibitor.

4. Method according to claim 3, wherein the inhibitor comprises a backbone, a peptide backbone or peptidomimetic backbone and a thiol reactive group able to form a covalent bond to the thiol group of the cysteine of the TG.

5. Method according to claim 4, wherein the inhibitor is a compound according to general formula [TGI1]:

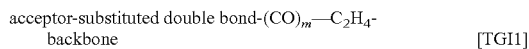

wherein m stands for 0 or 1 and the acceptor-substituted double bond carries at least one electron-drawing residue capable to conjugate with an electro negativity ≥2.20 and the backbone is a peptide or peptidomimetic from at least two amino acids or at least a dipeptidomimetic and/or the backbone shows at least one amide bond.

\* \* \* \* \*

UNITED STATES PATENT AND TRADEMARK OFFICE
CERTIFICATE OF CORRECTION

PATENT NO. : 8,808,980 B2  
APPLICATION NO. : 13/509225  
DATED : August 19, 2014  
INVENTOR(S) : Hils et al.

It is certified that error appears in the above-identified patent and that said Letters Patent is hereby corrected as shown below:

In the Claims:

Claim 1, col. 32, line 43, please delete "transglutaminase using the open form transglutaminase or antigenically" and substitute therefor --open form transglutaminase or antigenically--.

Signed and Sealed this  
Twenty-fifth Day of November, 2014

Michelle K. Lee  
*Deputy Director of the United States Patent and Trademark Office*